_US005725756A_

United States Patent [19]

Subramaniam et al.

[11] Patent Number: 5,725,756
[45] Date of Patent: Mar. 10, 1998

[54] IN SITU MITIGATION OF COKE BUILDUP IN POROUS CATALYSTS WITH SUPERCRITICAL REACTION MEDIA

[75] Inventors: Bala Subramaniam; Said Saim, both of Lawrence, Kans.

[73] Assignee: Center For Research, Inc., Lawrence, Kans.

[21] Appl. No.: 424,872

[22] Filed: Apr. 18, 1995

[51] Int. Cl.$^6$ ................................................ C10G 9/16
[52] U.S. Cl. ...................... 208/48 R; 208/83; 208/91; 585/820; 585/823; 585/824; 585/950
[58] Field of Search ........................ 208/48 R, 83, 208/91; 585/950, 820, 823

[56] References Cited

U.S. PATENT DOCUMENTS

| | | | |
|---|---|---|---|
| 4,176,045 | 11/1979 | Leftin et al. | |
| 4,243,831 | 1/1981 | Malloy et al. | |
| 4,338,448 | 7/1982 | Yellin et al. | 548/343 |
| 4,483,761 | 11/1984 | Paspek, Jr. | 208/106 |
| 4,605,811 | 8/1986 | Tiltscher | 585/670 |
| 5,030,788 | 7/1991 | Amelse et al. | |
| 5,221,462 | 6/1993 | Reid et al. | |

OTHER PUBLICATIONS

Tiltscher, Melmut et al.; "A Mild and Effective Method for the Reactivation or Maintenance of the activity of Heterogeneous Catalysts"; *Angew. Chem. Int. Ed. Engl.*, 20, (1981). No. 10, pp. 892–894.

Tiltscher, H. et al.; "Trends in High Pressure Chemical Reaction Engineering"; *Chem. Eng. Sci.*, vol. 42, No. 5, pp. 959–977, 1987.

Saim, Said et al.; "Phase and Reaction Equilibria Considerations in the Evaluation and Operation of Supercritical Fluid Reaction Processes"; *Supercritical Fluid Science and Technology;* Johnson, K.P. et al., Eds., ACS Symposium Series No. 406, pp. 301–316 (1989).

Saim, Said et al.; "Isomerization of 1-Hexene on Pt/γ-Al$_2$O$_3$ Catalyst at Subcritical and Supercritical Reaction Conditions: Pressure and Temperature Effects on Catalyst Activity"; *The Journal of Supercritical Fluids*, vol. 3, No. 4, pp. 214–221, 1990.

Manos, Georgios et al.; "Coke Removal from a Zeolite Catalyst by Supercritical Fluids", *Chem. Eng. Technol.*, 14 (1991) 73–78.

Saim, Said et al.; "Isomerization of 1-Hexene over Pt/γ-Al$_2$O$_3$ Catalyst: Reaction Mixture Density and Temperature Effects on Catalyst Effectiveness Factor, Coke Laydown, and Catalyst Micromeritics", *Journal of Catalysis*, 131, 445–456 (1991).

Baptist-Nguyen, Sarah et al.; "Coking and Activity of Porous Catalysts in Supercritical Reaction Media"; *AlchE Journal*, vol. 38, No. 7, pp. 1027–1037, Jul. 1992.

*Primary Examiner*—Helane Myers
*Attorney, Agent, or Firm*—Hovey, Williams, Timmons & Collins

[57] ABSTRACT

A method to minimize catalyst deactivation rate and coke laydown, and maximize desired reaction rate in processing of industrially significant reactions under supercritical conditions to generate a reaction mixture stream including formed reaction products and reactants, said contacting at a desired catalyst temperature of about 1–1.2 critical temperature of the resulting reaction mixture and at a pressure between the critical pressure of the reaction mixture and a pressure necessary to establish said reaction mixture fluid density of greater than 0.65 gm/cc.

14 Claims, 16 Drawing Sheets

IN SITU MITIGATION OF COKE BUILDUP IN POROUS CATALYSTS WITH SUPERCRITICAL REACTION MEDIA

FIELD OF THE INVENTION

The present invention broadly relates to the mitigation of coke formation on catalysts in contact with hydrocarbons at elevated temperatures and pressures. In particular, this invention relates to the in situ mitigation of coke buildup in porous catalysts with near-critical and supercritical reaction media.

BACKGROUND OF THE INVENTION

Many industrially significant catalytic reactions such as isomerization, disproportionation of aromatics and alkylation reactions on acid catalysts are characterized by catalyst deactivation due to coke build-up on the catalyst.

Coking of acid catalysts is typically caused by side reactions that involve mainly acid-catalyzed polymerization and cyclization of olefins that produce higher molecular-weight polynuclear compounds which undergo extensive dehydrogenation, aromatization and further polymerization. These products are generally termed as coke and have been characterized as either "consolidated" carbon deposits (that cannot be dissolved in organic solvents) or "mobile" deposits which are precursors of the consolidated deposits. For example, in the case of reforming catalysts, the mobile deposits are typically polyaromatic hydrocarbons.

The primary reasons for coke buildup leading to catalyst deactivation, are the relatively low volatilities of the mobile coke compounds that are initially formed in the low sub-critical densities (and hence low coke solubilizing power) of the gas-phase reaction mixture. The relatively low volatilities of the mobile coke compounds at gas phase reaction conditions results in the strong adsorption of these compounds on the catalysts leading to their progressive transformation to consolidated coke. The consolidated coke buildup eventually plugs the pores of the support matrix, in which the catalyst particles reside, and causes total deactivation of the catalyst. The coked catalyst must then be regenerated, typically by air oxidation of the coke exposing the catalyst to high temperatures (400°–500° C.), which can often cause thermal degradation of the catalyst.

Much has been reported in the literature on the subject of supercritical operational effects upon coke formation and extraction, and corresponding trends in catalyst deactivation and reaction kinetics. These teachings, however, are in many respects inapplicable to industrially significant catalytic reactions because they often overlook critical coke formation and extraction mechanisms, and mass transport effects on catalyst effectiveness and catalyst deactivation rates under supercritical conditions. For example, for 1-hexene reaction on a low activity, macroporous shell $\gamma$-$Al_2O_3$ catalyst (having an active specific surface of 4.95 $m^2/g$), Tiltscher et al. *Angew Chem. Int. Ed.* 20:892(1981) teaches that reactor operation at supercritical conditions leads to steady state catalyst activity maintenance. The teaching is inapplicable to industrially significant reactions because the study employed shell catalysts having a catalytically active specific surface of 4.95 $m^2/g$. The shell catalyst configuration was used apparently to avoid pore diffusion limitations for the purpose of studying coke extraction mechanism associated with supercritical fluids. Industrially significant reactions often require highly porous catalysts having effective surface areas greater than 150 $m^2/g$.

Tiltscher et al. *Chem. Engng. Sci.* 42:959 (1987) teaches that the regeneration of highly porous catalysts (500 $m^2/g$) by supercritical fluids involves a much more complex mechanism (when compared to that associated with the shell catalyst referenced above having low catalytically active specific surface) because of pronounced internal transport processes. This reference, however, teaches that catalyst activity in the subcritical range is higher than activity in the supercritical range (though the deactivation rate in the subcritical is also higher).

Saim and Subramaniam *J. Supercrit. Fluids* 3:214 (1990) and Saim and Subramaniam *J. Catal.* 131:445 (1991) investigated 1-hexene isomerization on a high activity, high surface area, commercial Pt/$\gamma$-$Al_2O_3$ catalyst in a 300 ml CSTR at near-critical temperatures (1.01 $T_c$ and 1.1 $T_c$). At both temperatures, the authors reported that end-of-run isomerization rates decrease with isothermal increases in pressure in the subcritical region and moderate supercritical regions, and increase with pressure in the dense supercritical region ($\rho_c > 1.7$). However, the catalyst deactivated with time even at supercritical conditions. These teachings are not applicable to industrially significant reactions because, as the authors noted, a significant portion of the catalyst activity was lost due to buildup of consolidated, unextractable coke during the subcritical phase of reactor fill-up. These references are also inapplicable to industrially significant reactions because it teaches that steady state catalyst activity conditions may be achieved, but at the expense of a lower reaction rate for the desired reaction.

Manos and Hoffman *Chem. Eng. Technol.* 14:73 (1991), based on coke desorption rates and thermodynamic analysis of the solubilities of model coke compounds (such as polyaromatic hydrocarbons) in SCFs, concluded that while complete in situ reactivation of a zeolite catalyst by SCFs is impossible, the catalyst deactivation rate can be reduced. The authors observed that only freshly formed coke precursors could be dissolved by the SCF reaction medium and confirmed that rapid start-up was essential to avoid the formation of consolidated, unextractable coke during the subcritical phase of pressure buildup. This reference does not teach that the deactivation rate can actually increase in supercritical regions for highly porous catalysts. Thus, this reference teaches that complete coke removal by supercritical fluids is impossible but that catalyst deactivation could be slowed down under supercritical conditions.

By developing a single-pore model for coke formation and in situ coke extraction, Baptist-Nguyen and Subramaniam, *AICHE J.*, 38:1027 (1992), show that for an isothermal increase in pressure along a near-critical isotherm (1.01 $T_c$), there exists an optimum pressure (i.e., reaction mixture density) at which catalyst activity is maximized. At lower densities, the catalyst undergoes deactivation due to a lack of coke extraction while at higher than optimum densities the catalyst activity decreases due to pore diffusion limitations in liquid-like reaction mixtures. This reference teaches that all coke is removed when operating beyond optimum conditions noted in this reference and that catalyst activity reaches a steady state value beyond optimum conditions.

Various processes are known to inhibit coke formation in other certain processing environments. For example, U.S. Pat. No. 4,176,045 discloses a process for the production of olefins by steam cracking, during which process coke deposits in cracking furnace tubes is minimized by the addition of low-coking hydrocarbon to fresh feed having a high-coking tendency.

U.S. Pat. No. 5,221,462 discloses a method for inhibiting the formation and deposition of coke on heated metal surfaces in contact with a hydrocarbon feed stock undergoing pyrolytic processing to produce lower hydrocarbon fractions where metal surfaces have a temperature of about 1600° F., which method comprises adding to the hydrocarbon feed stock being processed a coke inhibiting amount of dyhydroxybenzene compound.

Problems also arise during conventional reactor operations during start-up and shut-down procedures. Such procedures often lead to rapid coking (by the same mechanisms discussed above) and catalyst deactivation because these procedures expose the catalyst to subcritical reaction mixtures, therefore requiring either frequent catalyst regeneration or a continuous supply of fresh catalyst to the reactor.

Accordingly, the requirements are exceedingly stringent for successfully mitigating coke buildup on catalyst surfaces exposed to hydrocarbons at elevated temperatures and pressures.

SUMMARY OF THE INVENTION

The present invention overcomes the problems outlined above, and provides a process employing in situ mitigation of coke buildup in porous catalysts with supercritical hydrocarbon and oxygenates (between $C_1$–$C_{20}$) reaction media.

The invention is predicated upon the discovery that near-critical reaction mixtures provide an optimum combination of solvent and transport properties for the improved in situ extraction of coke-forming compounds (when compared to gas-phase reaction mixtures) and for the faster transport of reactants and products (when compared to liquid-like reaction mixtures). There exists an optimum temperature and pressure in the supercritical region at which the reaction rates of the desired reactions are maximized and catalyst deactivation rates are minimized. Although coke laydown progressively decreases in denser supercritical reaction mixtures, the desired reaction rates are lower and the catalyst deactivation rates are higher due to pore diffusion limitations in liquid-like reaction mixtures. In accordance with the instant invention, the hydrocarbon feed stock steam is contacted with a quantity of catalyst (having a total surface area greater than 5 m²/g) at the desired reactor temperature which is about 1–1.2 critical temperature of the resulting reaction mixture and at a pressure between the critical pressure of the reaction mixture and a pressure necessary to establish said reaction mixture fluid density of greater than 0.65 gm/cc, and preferably greater than 0.5 gm/cc. If necessary, inert cosolvents may be added to the feed stream such that the reactor temperature is indeed about 1–1.2 critical temperature of the resulting reaction mixture. The instant invention may be practiced with any industrially significant catalytic reaction which is subject to coking problems, including isomerization, disproportionation of aromatics, alkylation, and acylation reactions.

The invention is also predicated upon the discovery that the reduction in olefinic oligomer formation in the fluid phase in conjunction with enhanced in situ extraction of coke-forming compounds (as stated above) further reduces coke laydown and thereby further improves catalyst pore accessibilities and rates of desired reactions. Oligomers formed in the fluid phase are prolific coke precursors and become an important consideration in supercritical reaction operations because oligomer formation steadily increases with pressure. Oligomer formation can amount to as much as 2 wt % of effluent product streams at supercritical pressures corresponding to a reduced density of the reaction media in excess of about 1.7. It has been determined that any peroxide impurities (including organic and inorganic peroxides) present in the feed stock catalyze the formation of the oligomers. In accordance with the instant invention, therefore, oligomer formation in the fluid phase is substantially curtailed by removing peroxide impurities from the feed stock (to less than 100 ppm, preferably to less than 50 ppm in the feed stock stream) by means of on-line adsorption of peroxide impurities in a bed of activated alumina, or other suitable adsorption media. Such pretreatment of feed stock significantly improves catalyst performance, especially in near-critical and supercritical reaction mixtures.

In another aspect of the invention, exposure of the catalyst to subcritical reaction mixtures, typically experienced during start-up and shut-down procedures, is avoided to prevent formation of consolidated coke on the catalyst. Thus, in accordance with the instant invention during reactor start-up, desired operating temperatures are obtained by flowing only inert cosolvent (which cosolvents do not form coke on the catalyst), followed by the introduction of the actual feed stock to the catalyst-containing reactor. This start-up mode insures that the reaction mixture is already in a near-critical or supercritical state before the catalyst is exposed to the actual feed stock. During shut-down, the feed stock is once again switched to an inert cosolvent feed to flush the reactants from the reactor before depressurizing and cooling the reactor. Cosolvents employed with the instant invention have critical properties similar to those of the reaction mixture at reactor operating conditions. In particular, cosolvents useful in the practice of the invention have a critical temperature within 0.8–1.4 $T_c$ of the reaction mixture, and preferably within 1.01–1.2 $T_c$ of the reaction mixture and a critical pressure between 0.8–3.0 $P_c$, and preferably between 0.9–1.4 $P_c$ of the reaction mixture.

Separation of reaction products, reactants and inert cosolvents in the product stream is preferably accomplished by isothermal, stepwise, pressure reduction.

In accordance with the instant invention, reaction rates for the desired reactions and catalyst deactivation rates are substantially improved relative to operation with subcritical reaction mixtures. Catalyst life is substantially extended in industrially significant reactions.

In another aspect of the invention, a membrane reactor is employed to remove hydrogen generated from catalytic dehydrogenation of hydrocarbon feed stocks. The purpose of the hydrogen removal is to permit the attainment of liquid-like densities in supercritical product streams required for the enhanced in situ extraction of coke-forming compounds from dehydrogenation catalyst.

In yet another aspect of the invention, hydrogenation reactions use either a hydrocarbon solvent or a mixture of hydrocarbon solvents in the reaction mixture such that the desired catalyst temperature is 1.0–1.2 critical temperature of the reaction mixture exclusive of permanent gasses (e.g., $H_2$ and $CO_2$). Optimum pressure is between the critical pressure of the reaction medium and a pressure at which the density of the reaction medium is greater than 0.65 gm/cc. Product separation is performed by step-wise pressure reduction in a downstream separator.

DETAILED DESCRIPTION OF THE PREFERRED EMBODIMENTS

The following examples set forth preferred compositions and techniques for practicing the instant invention, as well as test results demonstrating effectiveness. It is to be understood, however, that these examples are presented by way of illustration only and nothing therein shall be taken as a limitation upon the overall scope of the invention.

EXAMPLE 1

Enhanced in Situ Extraction of Coke Compounds Attainable

Example 1 demonstrates that enhanced in situ extraction of coke compounds can be attained by near-critical and supercritical reactor conditions, thus preventing pore plugging that otherwise occurs at subcritical conditions when hydrocarbon feed stock is exposed to solid, porous acid catalyst. Example 1 also demonstrates that, although coke laydown continues to decrease in denser, supercritical reaction mixtures, isomerization rates are lower and catalyst deactivation rates are higher due to pore diffusion limitations in liquid-like reaction mixtures. Example 1 shows that near-critical reaction mixtures provide an optimum combination of solvent and transport properties for enhanced in situ extraction of coke-forming compounds (when compared to gas-phase reaction mixtures) and for the faster transport of reactants in products (when compared to liquid-like reaction mixtures).

Experimental Procedure

Figure 1:
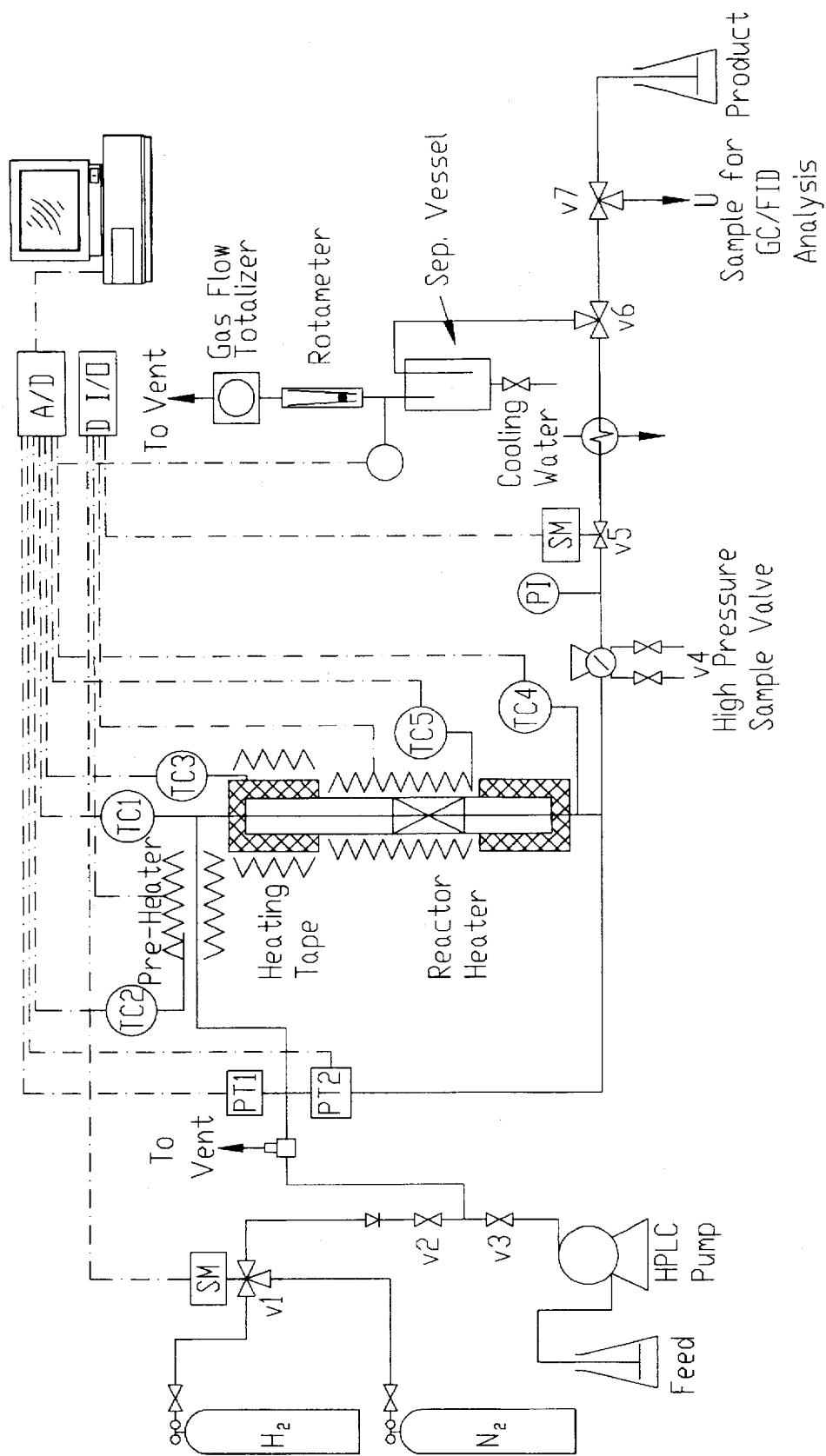
FIG. 1 is a schematic of the experimental unit used in Example 1.

The reaction of 1-hexene feed stock on $\frac{1}{16}$" Pt/$\gamma$-Al$_2$O$_3$ (Engelhard E-302-active specific surface area of 175 m$^2$/g) reforming catalyst extrudates was chosen as the test reaction. FIG. 1 shows a schematic of the reactor unit. A Waters' dual piston HPLC pump rated to provide flow rates between 6 and 600 ml/h with a pressure head up to 414 bar was used to feed 1-hexene (Ethyl Corporation; CAS # 592-41-6; Lot # 851201). By closing the liquid shut-off valve (V3) and opening the gas shut-off valve (V2), either hydrogen or nitrogen gas may be admitted to the reactor unit. The feed gas was selected by a three-way, computer-controlled solenoid valve (V1).

The reactor is a low volume (10 ml) stainless steel tubular reactor that permits rapid startup. With the reactor held at the operating temperature, the critical density was reached or passed in two minutes and the operating pressure was reached in less than three minutes in all supercritical density experiments. The reactor inlet pressure was measured with a high-pressure transducer (PT1; 345±1.8 bar). This measurement was used to set the position of the computer-actuated, step-ping-motor-driven micrometering valve (V5, an Autoclave Engineers' 30VRMM valve with C$_v$=0.004). A low-pressure transducer (PT2; 1.4±0.007 bar) was used to measure the pressure drop across the reactor. The thermocouple at the catalyst bed entrance (TC1) was used to control the preheater temperature (TC2) while the thermocouple at the catalyst bed exit (TC4) was used to control the reactor heater temperature (TC5). The reactor, tubing, valves and fittings were all made of Type 316 stainless steel providing a system working pressure of 690 bar at 25° C. Reactor effluent passed through the micrometering valve (V5), was cooled and then sampled (V7) for product analysis.

The catalyst was first pretreated in flowing nitrogen at 100 sccm in a pretreatment reactor at 330° C. for 18 hours, followed by hydrogen at 100 sccm at 330° C. for four hours. Catalyst coking and activity were investigated at 281° C. (1.1 $T_c$) and at several pressures that yielded reaction mixture densities that ranged from gas-like to liquid-like values as shown in Table 1. Because the reaction mixture contains mostly hexene and its isomers, the critical properties remain virtually constant with 1-hexene conversion. Typical catalyst loading was 1 g and the space velocity was roughly 135 g hexene/g cat/h for all the runs. At this feed rate, the isomerization rates were determined to be free of external mass transfer limitations.

TABLE 1

Operating pressures and corresponding reaction mixture densities: T = 281° C. (1.1 $T_c$)

| Pressure (bar) | *Density (kg/m³ × $10^{-3}$) | Reduced density |
|---|---|---|
| 21.7 | 0.050 | 0.21 |
| 35.5 | 0.101 | 0.42 |
| 52.7 | 0.204 | 0.85 |
| 70.0 | 0.287 | 1.20 |
| 139 | 0.412 | 1.72 |
| 222 | 0.475 | 1.98 |
| 277 | 0.502 | 2.09 |
| 346 | 0.528 | 2.20 |

*evaluated using Peng-Robinson equation of state [8].

An HP5890 GC/FID system was employed to measure the hexene isomers and high molecular weight coke precursors in the reactor effluent. Isomer formation rates and product selectivity were calculated from these measurements. At the end of each run (typically 8 hours), the catalyst was removed and characterized with respect to:

(a) the quantity of coke laydown by gravimetric analysis;
(b) the pore volume and surface area distributions by nitrogen physisorption; and (c) the Soxhlet extractability of the coke remaining in the catalyst.

RESULTS AND DISCUSSIONS

Coke Laydown, Isomerization/Deactivation Rates and Product Selectivity

Figure 2:
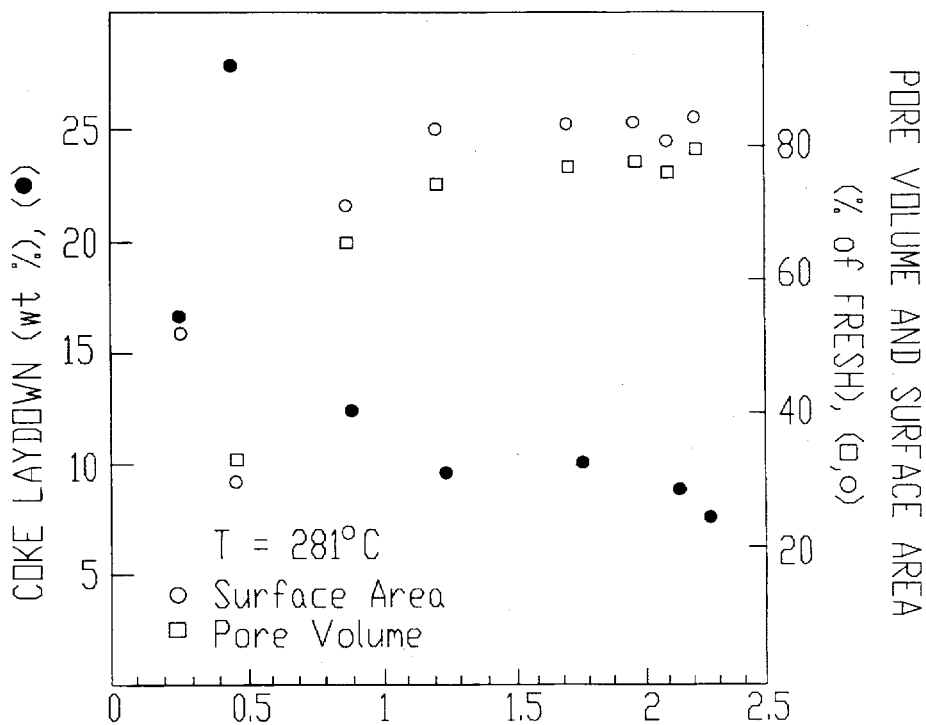
FIG. 2 is a plot showing end-of-run laydown, pore volume and surface area in sub- and supercritical reaction mixtures.

FIG. 2 shows the end-of-run coke laydown and remaining surface area/pore volume on catalysts exposed to subcritical, near-critical and supercritical reaction mixtures. At subcritical densities, there is virtually no in situ coke extraction and hence the coke laydown increases from roughly 17 wt % at $\rho_r$=0.27 to nearly 28 wt % at $\rho_r$=0.47. Consequently, 50–70% of the catalyst surface area and pore volume are lost. In near-critical ($\rho_r$=0.85) and supercritical mixtures, however, the coke laydown decreases to 13 wt % or less and more than 70% of the catalyst surface area and pore volume are maintained. These results provide evidence of in situ extraction of the coke-forming compounds from the catalyst pores by near-critical and supercritical reaction mixtures.

Figure 3:
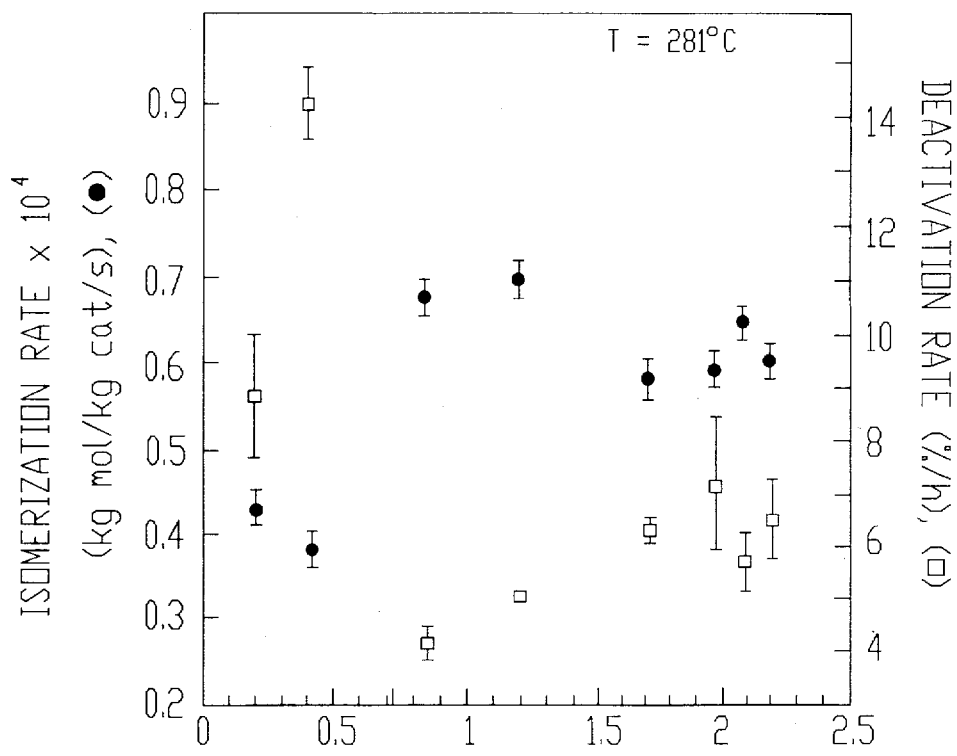
FIG. 3 is a plot showing end-of-run isomerization and deactivation rates in sub- and supercritical reaction mixtures.

As seen in FIG. 3, the end-of-run isomerization rates are highest and the deactivation rates (expressed as the % decrease in the isomerization rate between six and eight hours) are lowest in near-critical reaction mixtures. Although the end-of-run coke laydown decreases at supercritical conditions, the isomerization rates are lower due to increasing pore diffusion limitations at the higher densities. These results prove that near-critical reaction mixtures provide an optimum combination of solvent and transport properties for maximizing the isomerization rates and minimizing the deactivation rates.

Figure 4:
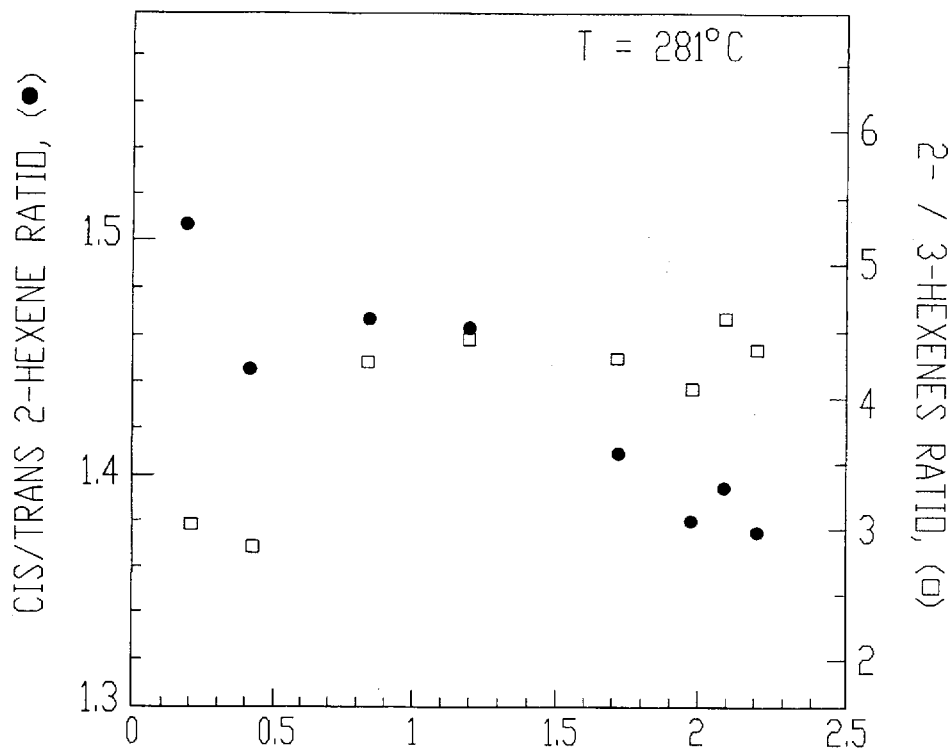
FIG. 4 is a plot showing end-of-run product selectivity in sub- and supercritical reaction mixtures.

FIG. 4 shows the variations of the end-of-run product selectivity with reaction mixture density at a fixed space velocity. The 2-/3-hexenes selectivity ratio follows the 1-hexene isomerization rate trend attaining the highest value at near-critical densities. Statistical analysis revealed that the change in this selectivity ratio is primarily correlated to the change in the isomerizaton rate or equivalently, to reactor operating conditions causing this change. In contrast, the cis/trans 2-hexene selectivity is highest at $\rho_r$=0.21 and lowest at $\rho_r$=2.2, and the variation in this selectivity is better correlated by the variation in reaction mixture density.

Pore volume distribution in coked catalysts and coke layer thickness

Figure 5:
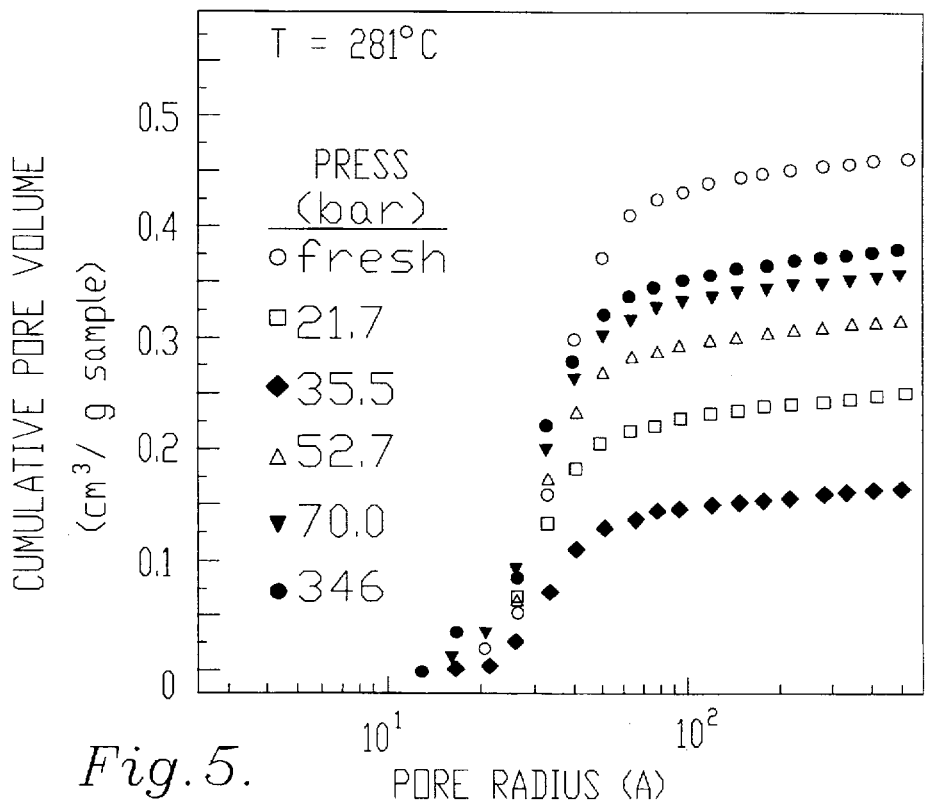
FIG. 5 is a plot showing pore volume distribution in coked and uncoked catalysts.

FIG. 5 shows the pore volume distributions (based on the nitrogen desorption isotherm) in the uncoked and coked catalyst samples. The measured pore radii ranged from 12–544 Å. Roughly 65% of the total pore volume of the uncoked catalyst, or 0.297 cc/g, resides in the 12–40 Å range. For the 8 h run at 35.5 bar ($\rho_r$=0.42), only 36% of the original pore volume in the 12–40 Å range (i.e., 0.108 cc/g) remained in those pores as compared to 78% at 52.7 bar ($\rho_r$=0.85) and 92% for catalysts coked in supercritical reaction mixtures. The decrease in volume in the 12–40 Å pores at subcritical conditions indicates plugging of the smaller pores (either by pore filling or pore mouth blockage) while the increase in volume in the 12–40 Å pores at near-critical and supercritical conditions suggests that these pores, while narrowed by coke laydown, may remain open.

Figure 6:
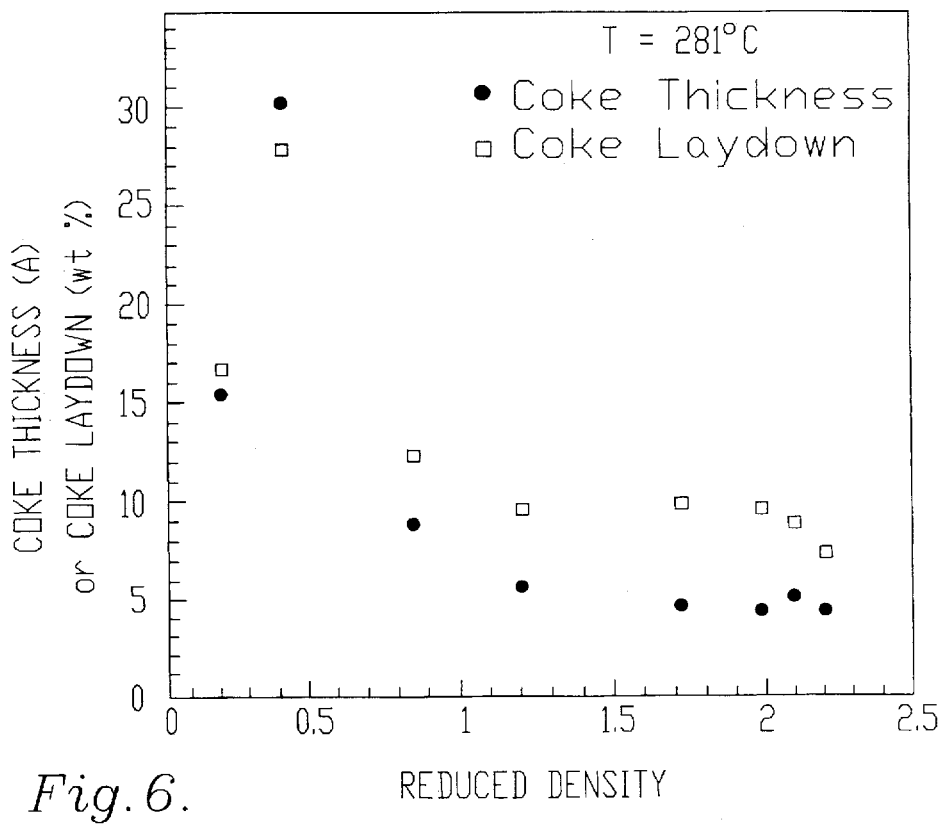
FIG. 6 is a plot showing amount of thickness of coke formed in sub- and supercritical reaction mixtures.

Assuming cylindrical pores, an average coke layer thickness was estimated from the measured pore volumes in the uncoked and coked catalysts. The pore size distribution in the uncoked catalyst was estimated based on the nitrogen desorption isotherm. As shown in FIG. 6, the variation of coke thickness with density is remarkably similar to the coke laydown trend. Given that the smallest pore radius measured is 12 Å, it follows that pores up to 16 Å and 30 Å are blocked in catalysts coked in subcritical reaction mixtures ($\rho_r$=0.21 and 0.42 respectively) and that all larger pores are lined with coke up to thicknesses of 16 and 30 Å. In contrast, all pores (including 12 Å pores) remain open in catalysts coked in near-critical and supercritical reaction mixtures. The coke thickness decreased continuously from 8.9 Å at $\rho_r$=0.85 to 4.2 Å at $\rho_r$=2.2. These results provide further evidence that near-critical and supercritical reaction mixtures alleviate pore choking and prevent pore plugging (during the eight hour run) by in situ extraction of the coke compounds.

Chemical nature of coke remaining on catalyst

Figure 7:
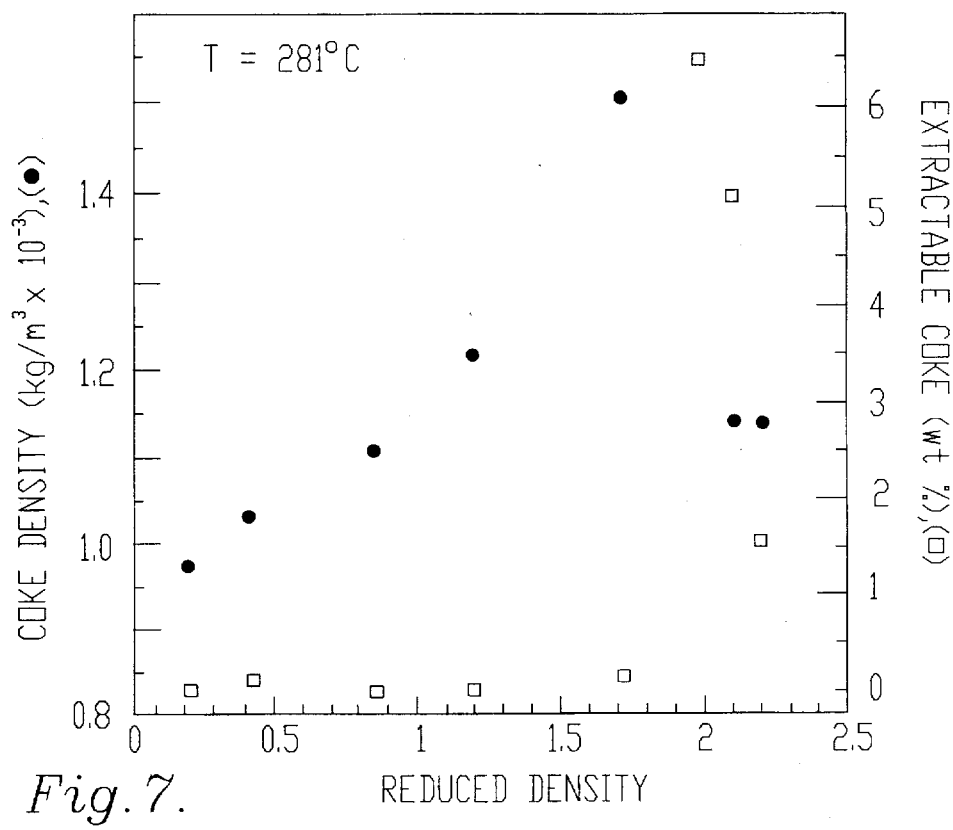
FIG. 7 is a plot showing density and Soxhlet-extractability of coke formed in sub- and supercritical reaction mixtures.

From the coke laydown and pore volume loss data, a coke density was estimated. As shown in FIG. 7, the coke density increases from 0.98 g/cc at $\rho_r$=0.21 to 1.5 g/cc at $\rho_r$=1.7, then decreases to 1.14 g/cc at $\rho_r$=2.2 indicating that the chemical nature of the coke deposits depends upon the operating conditions. A portion of the coked catalyst from each run was size-reduced and extracted with boiling toluene for 48 h in a Soxhlet extractor. As shown in FIG. 7, the Soxhlet-extractable coke (expressed as wt % of the amount of coke deposited on the catalyst during an entire run) was insignificant (less than 0.2 wt %) for catalysts coked in reaction mixtures at $\rho_r \leq 1.7$, increases significantly to 6.5 wt % at $\rho_r$=1.98, and then decreases to 5.2 wt % at $\rho_r$=2.1 and 1.6 wt % at $\rho_r$=2.2. The increased Soxhlet extractability of the coke formed in dense supercritical reaction mixtures (1.98<$\rho_r$<2.2) provides further evidence of a change in the coke chemistry in this density range.

Following the Soxhlet extraction, the toluene solution was concentrated and analyzed by GC/FID. The peaks had retention times ranging from the toluene solvent peak to greater than that of a $C_{30}$ olefin. The area percentages under peaks eluting from 5.5–21 mins (toluene-$C_{18}$ olefins), 21–31 mins ($C_{18}$–$C_{30}$ olefins), and 31–72 mins (>$C_{30}$ olefins) are compared in Table 2 for cases when the Soxhlet extractable coke was >0.1 wt %. It is seen that for the catalyst coked in the subcritical reaction mixture ($\rho_r$=0.42), a majority of the Soxhlet-extracted compounds had retention times less than $C_{30+}$ olefins with a significant portion in the toluene-$C_{18}$ range. The relatively large fraction of low volatility compounds demonstrates the inability of the subcritical reaction mixture to extract coke compounds in situ. In sharp contrast, the Soxhlet extract of catalysts coked in supercritical reaction mixtures had a majority of compounds in the $C_{30+}$ retention time range indicating effective in situ extraction of the low volatility coke compounds. This finding is consistent with the observed decreases in coke laydown on catalysts exposed to near-critical and supercritical reaction mixtures.

TABLE 2

Amount and type of compounds present in the Soxhlet extract of coked catalysts

| Reactor pressure (bar) | Reduced density | Soxhlet-extracted coke (wt %) | GC/FID peak area % of compounds in the Soxhlet extract of coked catalysts | | |
|---|---|---|---|---|---|
| | | | Toluene-$C_{18}$ | $C_{18}$–$C_{30}$ | $C_{30+}$ |
| 35.5 | 0.42 | 0.16 | 46.1 | 17.0 | 36.9 |
| 139 | 1.72 | 0.14 | 9.4 | 36.1 | 54.5 |
| 222 | 1.98 | 6.5 | 4.3 | 26.0 | 69.7 |
| 277 | 2.09 | 5.2 | 0.3 | 32.0 | 67.7 |
| 346 | 2.20 | 1.6 | 7.5 | 17.0 | 75.5 |

To gain insights into the chemical nature of the coke formed, the end-of-run catalyst samples from a subcritical experiment (21.7 bar) and from a supercritical run (222 bar) were analyzed by Temperature Programmed Oxidation (TPO) following the method of Barbier et al., *Reat. Kin. Cat. Lett.*, 29:323 (1985). A Bomem TG/plus TGA equipped with an FTIR detector was used for the TPO analysis. The coke was oxidized in a stream of flowing oxygen (10 vol % in He) while the temperature was ramped from 150°–700° C. at a rate of 30° C./min. As noted in Table 3, the weight loss at total coke oxidation was in good agreement with the coke laydown measured gravimetrically. The TPO results show that the supercritical reaction mixture is able to better remove coke from the $Al_2O_3$ support sites that are responsible for the isomerization activity. It can be inferred from the H/C ratios that the coke formed in the supercritical reaction mixture is more hydrogenated relative to that formed in the subcritical reaction mixture. Consequently, the coke in the former case is completely oxidized at temperatures that are 80° C. lower.

TABLE 3

TPO results for catalysts coked in sub- and supercritical reaction mixtures

| | P = 21.7 bar $\rho_r$ = 0.21 | P = 222 bar $\rho_r$ = 1.98 |
|---|---|---|
| Coke Laydown (wt %) | 16.8 | 9.5 |
| TPO weight loss (wt %) | 17.5 | 9.8 |
| Coke on Pt site (wt %) | 4.1 | 5.3 |

TABLE 3-continued

TPO results for catalysts coked in sub- and supercritical reaction mixtures

| | P = 21.7 bar $\rho_r$ = 0.21 | P = 222 bar $\rho_r$ = 1.98 |
|---|---|---|
| Coke on $Al_2O_3$ support (wt %) | 13.4 | 4.5 |
| H/C ratio (molar) | 1.50 | 1.88 |

The higher H/C ratio indicates that dehydrogenation to form consolidated coke is retarded in supercritical reaction mixtures. Recent studies report that tetralin in supercritical toluene provides hydrogen transfer to the coal while the supercritical toluene by itself is a non-reactive solvent. One such study also states that the hydrogen transfer from tetralin increased with solvent density. Since transition metals are known to catalyze hydrogen transfer from supercritical solvents such as n-pentane [11, 12], it is conceivable that the supercritical reaction mixture acted as a hydrogen donor in the presence of the Pt metal given that olefins, dienes and aromatics are known to undergo hydrogenation-dehydrogenation reaction on the metal sites of a reforming catalyst. Hence, as reaction mixture density is increased in the supercritical region, the Soxhlet-extractable coke at the end of a run is expected to increase as more-hydrogenated coke is formed and then decrease due to a greater ability of the supercritical reaction mixture to hydrogenate and therefore extract the coke-forming compounds in situ from the catalyst. This hypothesis is consistent with the marked decreases in coke laydown and in coke layer density in catalysts exposed to dense supercritical reaction mixtures (1.7<$\rho_r$<2.2).

TABLE 4

Comparison of coked catalyst characteristics for different-size catalyst particles

| Operating conditions | Catalyst Property | Values for 0.15–0.29 mm particles | Values for 0.71 mm cylinders |
|---|---|---|---|
| 21.7 bar, ($\rho_r$ = 0.208) | Coke laydown (wt %) | 19.7 | 16.8 |
| | Surface area (m²/g) | 80.7 | 93.1 |
| | Pore volume (cm³/g) | 0.209 | 0.230 |
| 70 bar, ($\rho_r$ = 1.20) | Coke laydown (wt %) | 10.6 | 9.5 |
| | Surface area (m²/g) | 146.3 | 145.6 |
| | Pore volume (cm³/g) | 0.322 | 0.333 |
| 220 bar, ($\rho_r$ = 1.98) | Coke laydown (wt %) | 7.7 | 8.5 |
| | Surface area (m²/g) | 147.8 | 147.0 |
| | Pore volume (cm³/g) | 0.337 | 0.343 |

Catalyst particle size effects

Table 4 compares the end-of-run coke laydown, BET surface area, and pore volume for identical runs with the 0.71 mm cylindrical extrudates (as received) and size-reduced catalyst particles. For the subcritical density experiment, the end-of-run coke laydown had increased 17%, surface area had decreased 13% and pore volume had decreased 9% for the smaller catalyst particles. Also, the end-of-run isomerization rate was 31% higher in the latter case. These results indicate that the catalyst size-reduction mitigated pore-diffusion resistances, leading to higher reaction rates and allowing greater accessibility of coke-precursors into the catalyst. Thus, the dominant deactivation mechanism in the larger catalyst particles at subcritical densities appears to be indirect site suppression. For the near-critical and supercritical density experiments, the coked catalyst properties and eight-hour reaction rates were nearly similar for the original and size-reduced particles, with less than 1% variation in surface area and approximately 2% variation in pore volume. The difference in coke laydown is not significant when compared to the standard deviation of 0.5 wt %. The lack of significant change in these measured properties with catalyst size strongly suggests deactivation by direct site suppression in near-critical and supercritical reaction mixtures, and hence relatively uniform coke laydown across the pore-length. These results are consistent with the pore volume distributions in coked catalysts (see FIGS. 5 and 6, and discussions thereof) showing the alleviation of pore choking by near-critical and supercritical reaction mixtures.

CONCLUSIONS

Near-critical reaction mixtures provide an optimum combination of solvent and transport properties that is better than that of either subcritical (gas-like) or dense supercritical (liquid-like—>0.65 g/cc) mixtures for maximizing reaction rates and minimizing deactivation rates and coke laydown rates associated with hydrocarbon contact with acid catalyst. The catalyst employed with the invention includes micro, meso and macro catalysts. Intermediate products seem to be generally favored at near-critical conditions due likely to enhanced desorption of the product species. By in situ extraction of the coke-forming compounds, near-critical and supercritical reaction mixtures are able to alleviate pore choking and better maintain accessible catalyst surface area and pore volume.

In accordance with the invention, catalyst deactivation rate and coke laydown rate is minimized and the reaction rate of the desired reaction is maximized in hydrocarbon processing by operating under conditions such that the hydrocarbon feed stock is contacted with a quantity of solid, porous catalyst under supercritical conditions to form a product stream including reaction products and hydrocarbon reactants, at a desired catalyst temperature which is a near-critical temperature, preferably within about 1.01–1.2 critical temperature, of the product stream components and at a pressure between critical pressure of the stream components and a pressure necessary to establish a fluid density of the product stream greater than 0.65 g/cc, and preferably greater than 0.5 g/cc. As used herein, the term "desired catalyst temperature" means the desired operating temperature range for a particular catalyst and reactor.

Coke formed in dense supercritical reaction mixtures is more hydrogenated relative to coke formed in subcritical reaction mixtures indicating that dehydrogenation to form consolidated coke is retarded at supercritical conditions. Catalytic reactions that require liquid-like reaction media for coke extraction and/or heat removal, yet gas-like diffusivities for enhanced reaction rates can benefit from the use of near-critical reaction media that provide an optimum combination of these properties. The Fischer-Tropsch synthesis is an example of a reaction that has been shown to benefit from operation with supercritical reaction media.

EXAMPLE 2

Olefinic Oligomer and Cosolvent Effects on Coking and Activity of a Reforming Catalyst in Supercritical Reaction Mixtures Example 2 demonstrates that the reduction of oligomer formation in the fluid phase will yet further improve coke laydown, reaction rates of desired reactions, and catalyst deactivation rates when employed in conjunction with the enhanced in situ extraction of coke compounds by near-critical and supercritical reaction mixtures (as demonstrated above in Example 1).

EXPERIMENTAL PROCEDURES

The reaction of 1-hexene on $1/16''$ Pt/$\gamma$-Al$_2$O$_3$ (Engelhard E-302) reforming catalyst extrudates was studied in a low volume (10 ml) stainless steel tubular reactor that permits rapid startup. With the reactor held at the operating temperature, the critical density was reached or passed in two minutes and the operating pressure was reached in less than three minutes in all supercritical density experiments. The reactor operating pressure was controlled with a computer-actuated, stepping-motor-driven micrometering valve.

The Pt loading on the catalyst is 0.6 wt %. The catalyst was first pretreated in flowing nitrogen at 100 sccm in a pretreatment reactor at 330° C. for 18 hours, followed by hydrogen at 100 sccm at 330° C. for four hours. The pretreated catalyst was found to have a BET surface area of 175 m$^2$/g, total pore volume of 0.44 cm$^3$/g and an average pore radius of roughly 50 Å. Oligomer formation with and without the catalyst was investigated at 281° C. (1.1 T$_c$) and at several pressures that yielded reaction mixture densities ranging from gas-like to liquid-like values as shown in Table 5. Because the reaction mixture contains mostly hexene and its isomers, the critical properties remain virtually constant with 1-hexene conversion. For the catalytic runs, typical catalyst loading was 1 g and the space velocity was roughly 135 g hexene/g cat/h. By performing experiments at various hexene feed rates, it was found that the isomerization rates are free of external mass transfer limitations at the chosen space velocity.

TABLE 5

Operating Conditions for Oligomer Formation Studies at 281° C. (1.1T$_c$)

| Pressure (bar) | Density (g/cc)* | Reduced density |
|---|---|---|
| 21.7 | 0.050 | 0.21 |
| 35.5 | 0.101 | 0.42 |
| 52.7 | 0.204 | 0.85 |
| 70.0 | 0.287 | 1.20 |
| 139 | 0.412 | 1.72 |
| 222 | 0.475 | 1.98 |
| 277 | 0.502 | 2.09 |
| 346 | 0.528 | 2.20 |

*Evaluated using Peng-Robinson equation of state.

In order to decrease the coke-precursor concentrations while maintaining the solubility of coke-forming compounds in the supercritical reaction mixture, a set of constant density experiments was performed by adding various proportions of an inert cosolvent to the hexene feed. The experiments were performed at 281° C. with 1 g of catalyst at a feed flow rate of approximately 135 g/h. The operating pressures and densities for various cosolvent fractions are summarized in Table 6. The inert cosolvents chosen were n-pentane (P$_c$=29.7 bar; T$_c$=197.2° C.) and n-hexane (P$_c$= 33.4 bar; T$_c$=233.7° C.). These solvents did not show either measurable reaction or coke laydown at a space velocity 135 g/h/g cat after three hours of operation at 281° C. and a pressure that yielded a reaction mixture density of 0.47 g/cc (318 bar in the case of n-pentane and 229 bar for n-hexane). Most of the runs were made with n-pentane as the cosolvent. The n-pentane fraction in the binary feed was varied from none to roughly 80 mole %. For each run, the operating pressure was varied to yield a supercritical density of 0.47 g/cc, equivalent to that with neat 1-hexene feed at 222 bar and a density of 1.98 $\rho_c$. To obtain insights into cosolvent type and density effects, two additional runs were made at 50% cosolvent addition: one retaining n-pentane as a cosolvent but at a reduced pressure yielding a lower density of 0.29 g/cc (equivalent to the run without cosolvent addition at 70.0 bar with a density of 1.20 $\rho_c$) and the other with n-hexane instead of n-pentane added as a cosolvent at a density of 0.47 g/cc. Due to insufficient availability of 1-hexene from lot# 851201, approximately 35% of the hexene feed used in the n-hexane cosolvent experiment was from lot# PT 060592.

TABLE 6

Operating Conditions for Cosolvent Effect Studies

| Cosolvent | Cosolvent fraction in feed (mole %) | Pressure (bar) | Density[a] (g/cc) | Run time (h) |
|---|---|---|---|---|
| None | — | 222 | 0.475 | 10 |
| n-pentane | 23.5 | 242 | 0.475 | 8 |
| n-pentane | 49.2 | 265 | 0.475 | 8 |
| n-pentane | 82.0 | 296 | 0.474 | 10, 14 |
| n-pentane | 48.8 | 86.5 | 0.289 | 8 |
| n-Hexane[b] | 52.2 | 226 | 0.474 | 8 |

[a]Estimated using the Peng-Robinson equation of state.
[b]1-Hexene feed contained 35% 1-hexene from Lot Pt 060592.

An HP5890 GC/FID system was employed to measure the hexene isomers and oligomers in the reactor effluent. A Nermag R10-10 GC/MS system was used for structural identification of the hexene oligomers. Isomer formation rates, oligomer content and product selectivity were calculated from these measurements. At the end of each run (typically 8 hours), the catalyst was removed and characterized with respect to: (a) the quantity of coke laydown by gravimetric analysis; and (b) the pore volume and surface area distributions by nitrogen physisorption.

RESULTS AND DISCUSSION

Oligomer formation and its effects on catalyst activity and coking

Figure 8:
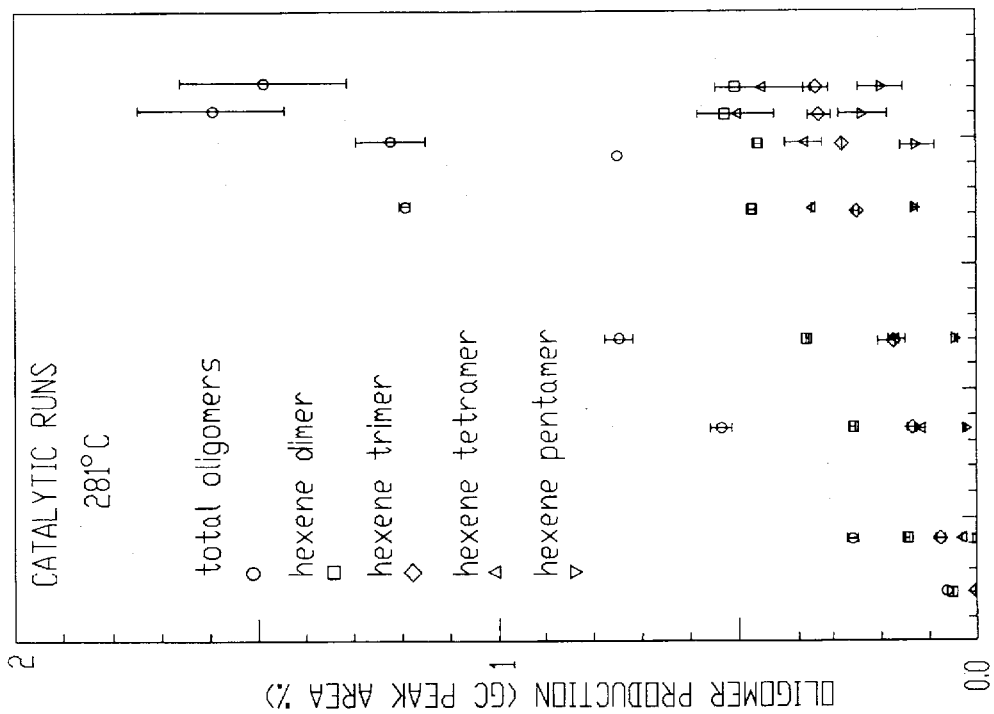
FIG. 8 is a plot showing hexene oligomer production for catalytic runs.

The amounts of hexene oligomers in the effluent of the catalytic and blank runs were measured as a function of reaction mixture density. FIG. 8 shows the production of the hexene oligomers for the catalytic runs based on samples collected from 6 to 8 hours of operation. The oligomer production plotted in FIG. 8 (and also in FIGS. 2 and 4) is a measure of the oligomer concentration in the reactor effluent. The GC area % represents the fraction of the total area under the various oligomer peaks, the hexene isomer peaks, the unreacted hexene peak and any inert cosolvent peak.

Figure 9:
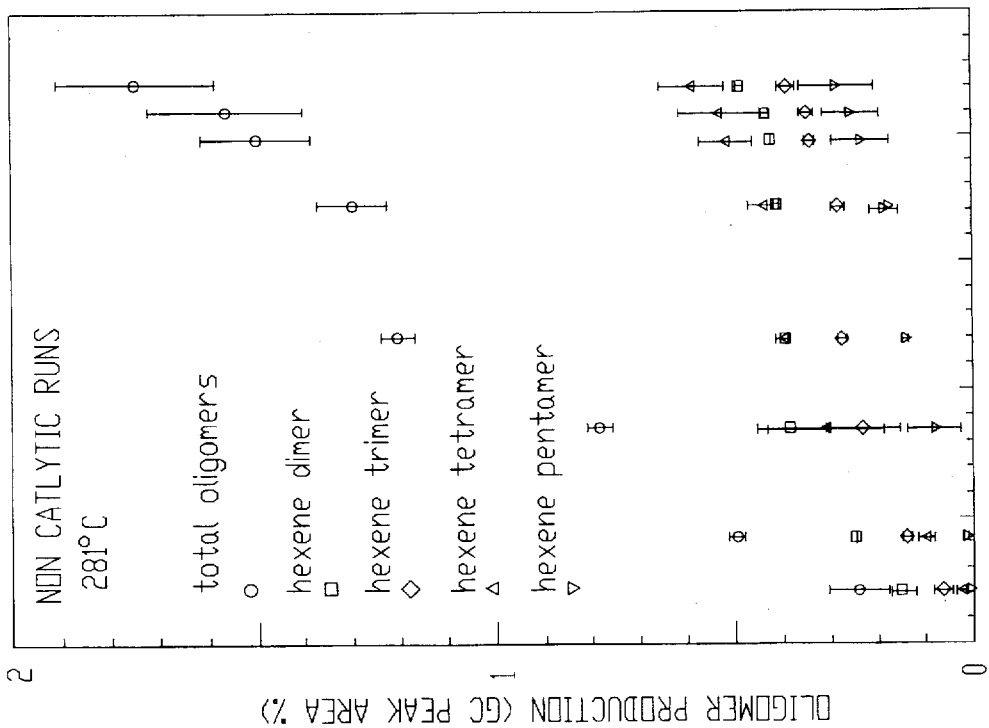
FIG. 9 is a plot showing hexene oligomer production in the absence of catalyst.

The amounts of the various hexene oligomers (dimer, trimer, tetramer and pentamer) are seen to increase with isothermal increases in density. The total oligomer production was relatively minor at subcritical densities (0.064% at 0.208 $\rho_c$), but increased almost linearly by about 25 fold at a supercritical density of 2.09 $\rho_c$. As seen in FIG. 9, a similar behavior of oligomer production was seen in the blank runs performed in the absence of catalyst. Total oligomer production at 0.208 $\rho_c$ was 0.24% and increased linearly with density to a maximum of 1.75% at 2.20 $\rho_c$. In both the catalytic and the blank runs, the average molecular weight of the oligomers increased with reaction mixture density. For the catalytic runs, the average oligomer molecular weight increased roughly 50% from 183 AMU at 0.208 $\rho_c$ to 272 AMU at 2.20 $\rho_c$. In the absence of catalyst, the average oligomer molecular weight increased 36% from 210 AMU at 0.208 $\rho_c$ to 284 AMU at 2.20 $\rho_c$. Tests for possible catalytic activity due to the reactor material of construction revealed that the oligomer formation rate was proportional to the residence time based on the homogeneous reactor volume and not on the reactor surface area. Virtually all the oligomer formation therefore occurred in the fluid phase.

The end-of-run (8 h) isomerization rates, the end-of-run deactivation rates (expressed as the % decrease in the isomerization rate between six and eight hours of operation) and coked catalyst properties corresponding to the catalytic runs were reported in Example 1.

Despite the higher concentration of coke-forming oligomers in supercritical reaction mixtures, the isomerization rates were higher and deactivation rates were lower when compared to subcritical reaction mixtures. This is attributed to the enhanced desorption of coke-forming oligomers in higher density reaction mixtures. Comparing FIGS. 8 and 9, it can be seen that at the lowest subcritical density, the total oligomers in the reactor effluent were almost fourfold lower in the presence of the catalyst when compared to the blank run. In contrast, the corresponding decrease at the highest supercritical density was only 10%. These results indicate that while the oligomers formed in the fluid phase adsorb strongly on the catalyst surface at subcritical conditions leading to increased coke formation, near-critical and supercritical reaction mixtures favor desorption of the oligomers.

Coke formation on acid catalysts is believed to involve the polymerization and cyclization of olefins on the catalyst surface to yield higher-molecular-weight polynuclear compounds. These undergo extensive dehydrogenation, aromatization and further polymerization to form "coke". The formation of oligomers in the bulk fluid phase would therefore be an added detriment to catalyst activity. To investigate the effect of oligomers on catalyst coking, an experimental run was performed in which a known amount of oligomers was added to the hexene feed. For this purpose, the effluent stream collected from the blank run at 281° C. and 277 bar, containing mostly 1-hexene and roughly 1.6 wt % oligomers, was used as the feedstock. This feed was introduced at 123 g/h to the reactor containing 1 g of pretreated catalyst. The reactor was operated at 281° C. and 21.7 bar, yielding a reduced reaction mixture density of 0.208.

Figure 10:
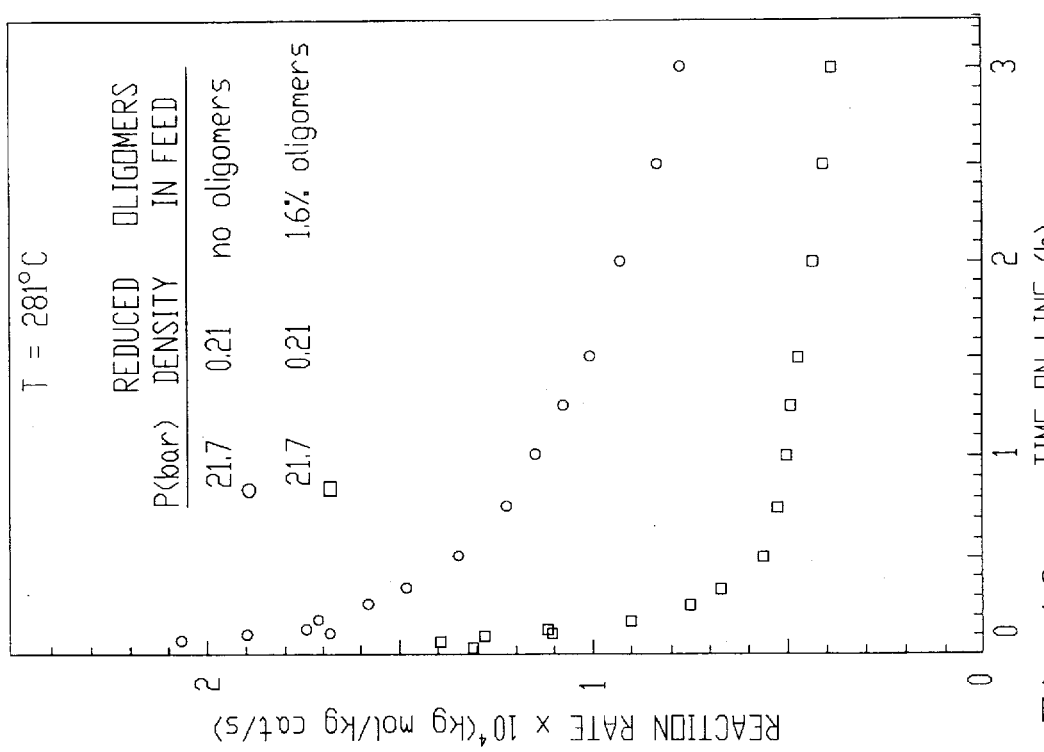
FIG. 10 is a plot showing a comparison of isomerization rate histories with no added oligomers and 1.6 wt % oligomers added to the feed.

A comparison of the isomerization rate histories for runs performed with and without added oligomers is shown in FIG. 10. The isomerization rate is computed as the measured conversion of 1-hexene to its isomers (2- and 3-hexenes) times the space velocity. For the experiment with 1.6 wt % oligomers in the feed: (i) the initial reaction rate was roughly a third relative to experiments with no oligomers; (ii) the three-hour isomerization rate was roughly one-half of the rate obtained with no added oligomers in the feed; and (iii) the isomerization rate declined in less than 15 minutes to a value observed at 3 hours for the experiment where no oligomers were added. In other words, the catalyst deactivation rate was twelve times faster when 1.6 wt % oligomers were present in the feed. From Table 7, it is seen that the addition of oligomers to the feed increased coke laydown by 35%, decreased catalyst surface area by 55% and catalyst pore volume by 41%. Clearly, the hexene oligomers formed in the fluid phase are significant coke precursors and accelerate catalyst deactivation.

TABLE 7

Effect of Feed Oligomers on Properties of Catalyst Coked at 281° C. and 21.7 bar

| Catalyst Property | Pretreated Catalyst | No Added Oligomers | 1.6 wt % Oligomers |
| --- | --- | --- | --- |
| Coke laydown (wt %) | — | 16.8 | 22.7 |
| BET Surface area ($m^2/g$) | 174.9 | 93.1 | 42.1 |
| Pore volume (cc/g) | 0.440 | 0.230 | 0.136 |

Effects of Cosolvent Addition

While the increase in 1-hexene concentration over the experimental pressure range was roughly an order of magnitude (see Table 5), the corresponding increase in oligomer production was over two orders of magnitude (see FIGS. 8 and 9). Yet, in the near-critical and supercritical density range, reaction mixture density (which controls coke-compound solubility) increased by only twofold (see Table 5). In order to decrease the coke-precursor (i.e., hexene oligomer) concentrations while maintaining the in situ extraction of the coke-forming compounds, a set of constant density experiments was performed in which an inert cosolvent was added as explained in the experimental section.

The oligomer formation in the cosolvent runs, measured from 6 to 8 hours of operation, is shown in FIG. 8. Total oligomer production decreased sixfold from 1.2% in the absence of cosolvent to 0.2% with 80 mole % n-pentane in the feed. At approximately 50 mole % n-pentane addition, hexene oligomer production decreased as expected at the lower density of 0.29 g/cc. We also observed lower oligomer production when n-hexane instead of n-pentane was employed as the cosolvent. This result was puzzling at first since in both cases, the cosolvent fraction (50 mole %) and reaction mixture density (0.47 g/cc) were identical. As discussed in the next section, we later determined that the 1-hexene from Lot# PT 0605921 (that makes up 35% of the 1-hexene in the n-hexane cosolvent run) produced lower amounts of oligomers than the 1-hexene from lot# 851201 that was used in the runs with n-pentane as the cosolvent.

Figure 13:
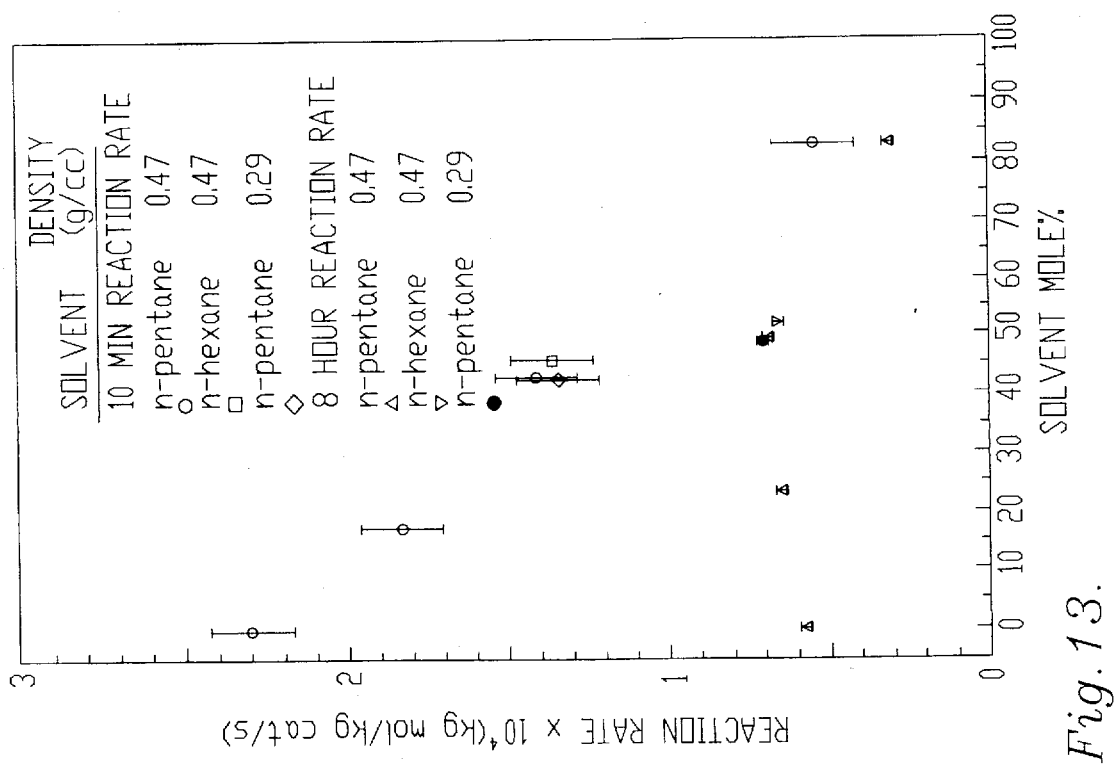
FIG. 13 is a plot showing cosolvent effect on initial and end-of-run isomerization rates.
Figure 12:
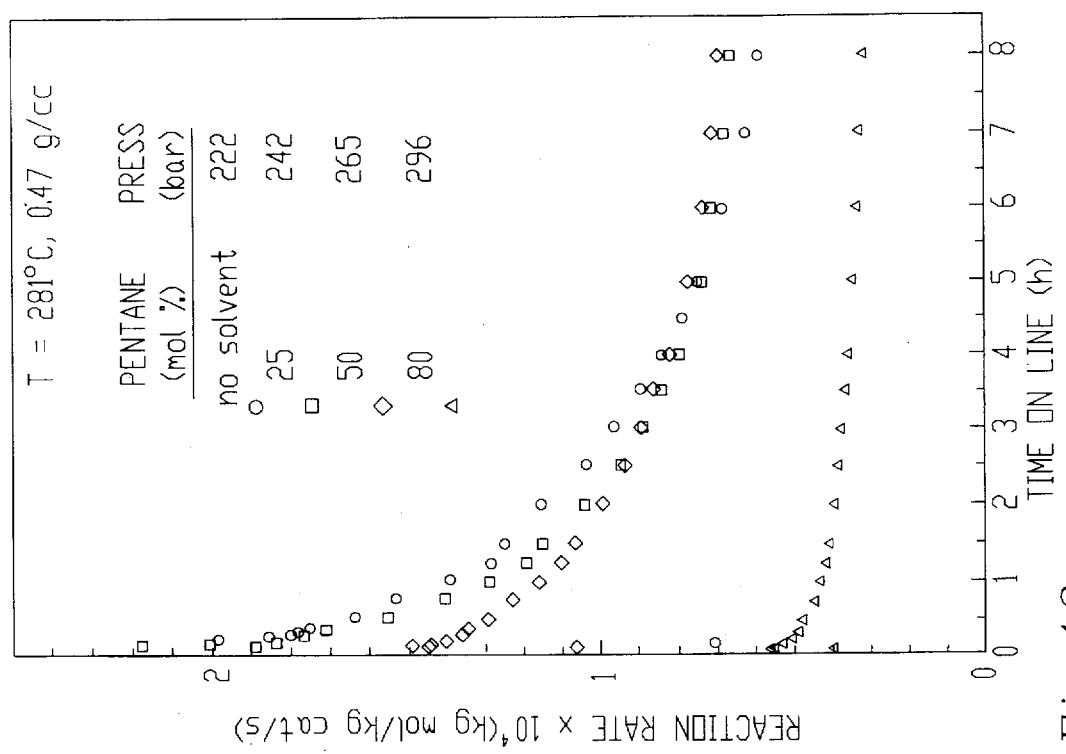
FIG. 12 is a plot showing cosolvent effect on isomerization rate histories.
Figure 14:
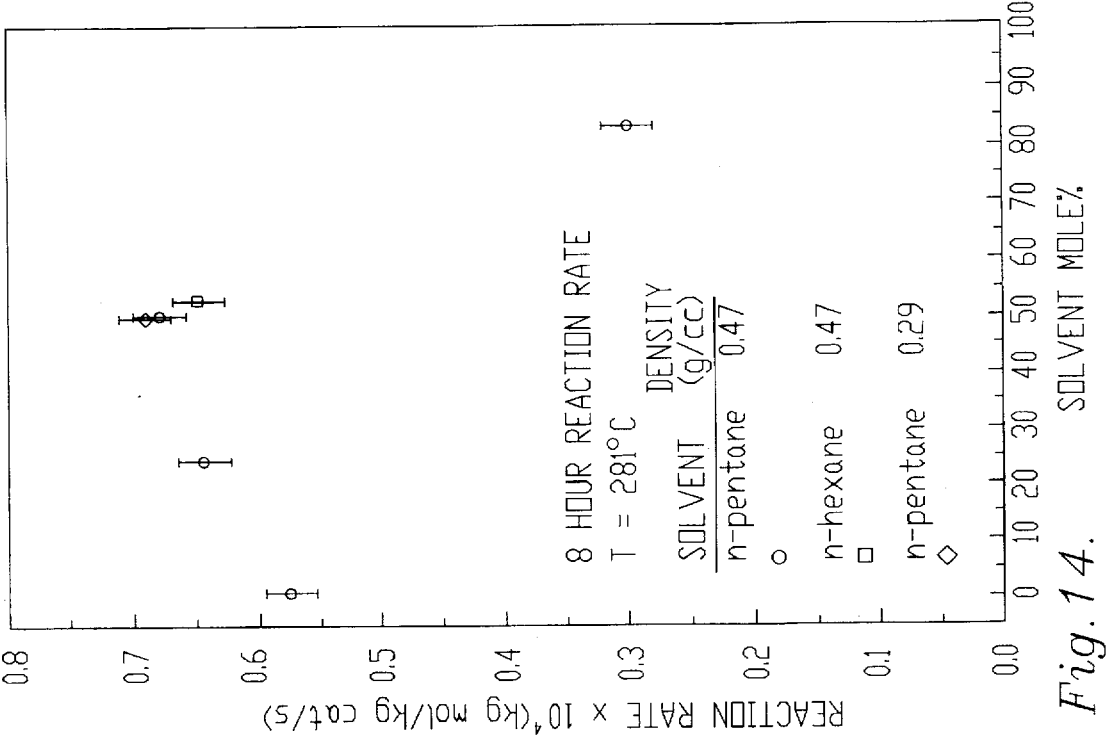
FIG. 14 is a plot showing cosolvent effect on end-of-run isomerization rates.
Figure 16:
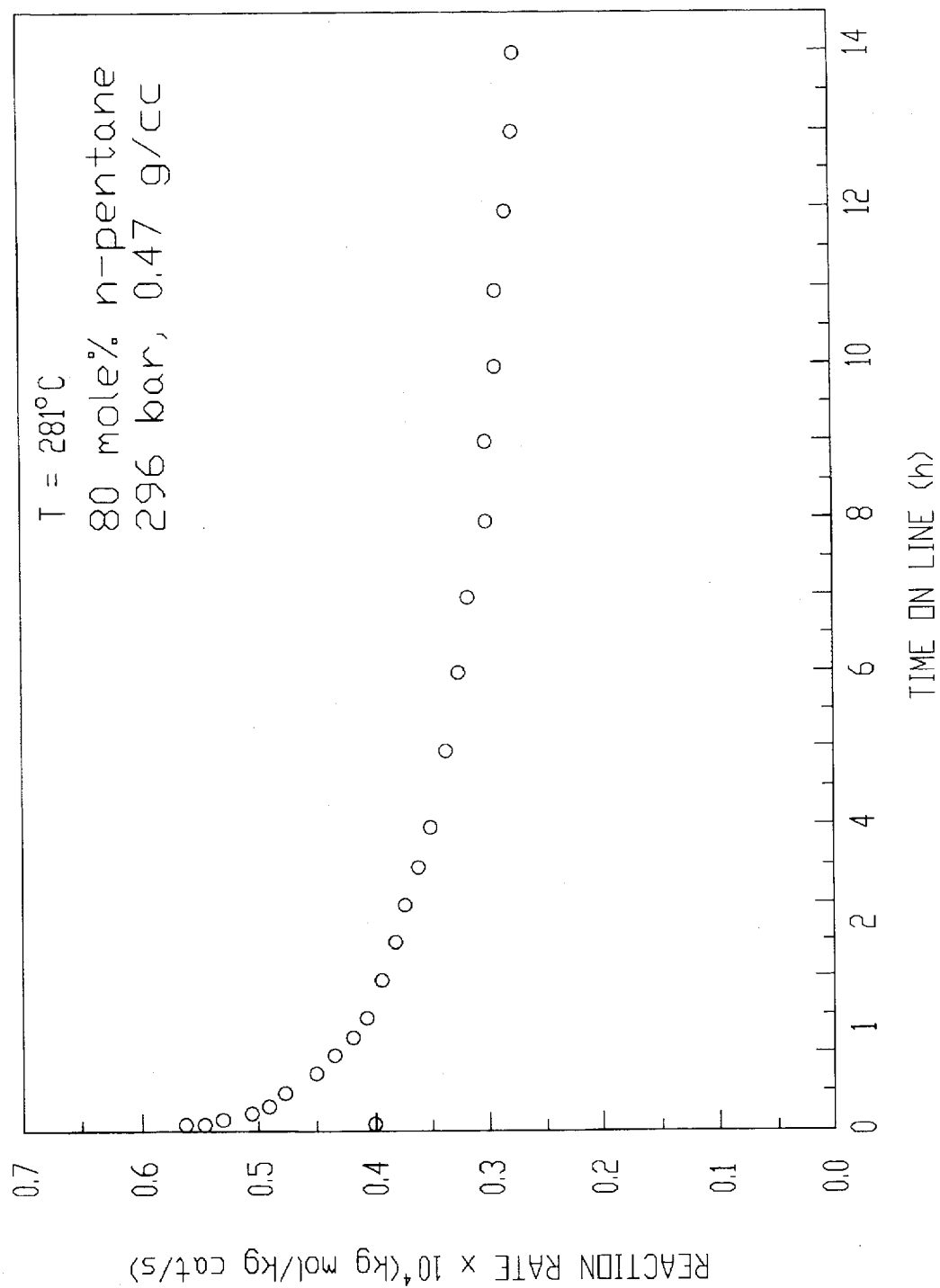
FIG. 16 is a plot showing temporal isomerization rates during an extended run with cosolvent.
Figure 18:
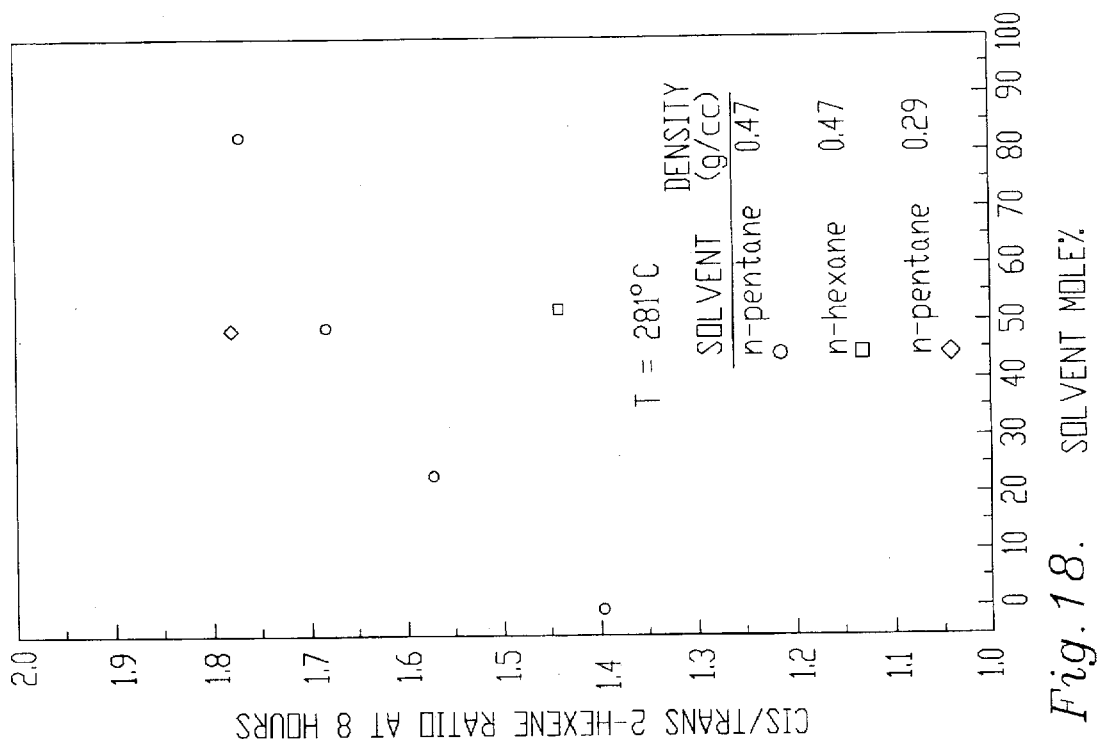
FIG. 18 is a plot showing cosolvent effect on cis-2/trans-2-hexene selectivity.

FIG. 12 shows the effect of an inert cosolvent addition on hexene isomerization rate histories. The initial (10 min.) isomerization rates decreased as expected when the n-pentane fraction in the feed is increased. In contrast, the rates at later run times (>6 h) showed a crossover. FIG. 13 shows the initial and end-of-run (8 h) isomerization rates as a function of n-pentane addition at a constant density of 0.47 g/cc. While the initial reaction rate decreased nearly fourfold with n-pentane addition up to 80 mole %, the end-of-run reaction rates increased with n-pentane addition up to 50 mole % and then decreased. This trend is seen more clearly in FIG. 14. The increase in reaction rate despite the decrease in 1-hexene concentration is attributed to the reduction in oligomer formation (and hence in the deactivation rate) with cosolvent addition while maintaining the in situ extraction of the coke-forming compounds. Even though the oligomer production continues to decrease at higher cosolvent fractions (>0.5), the isomerization rate eventually becomes limited by 1-hexene concentration and hence decreases. At roughly 50 mole % cosolvent addition, neither the decrease in reaction mixture density nor the substitution of n-hexane as the cosolvent significantly affects the isomerization rates.

Figure 15:
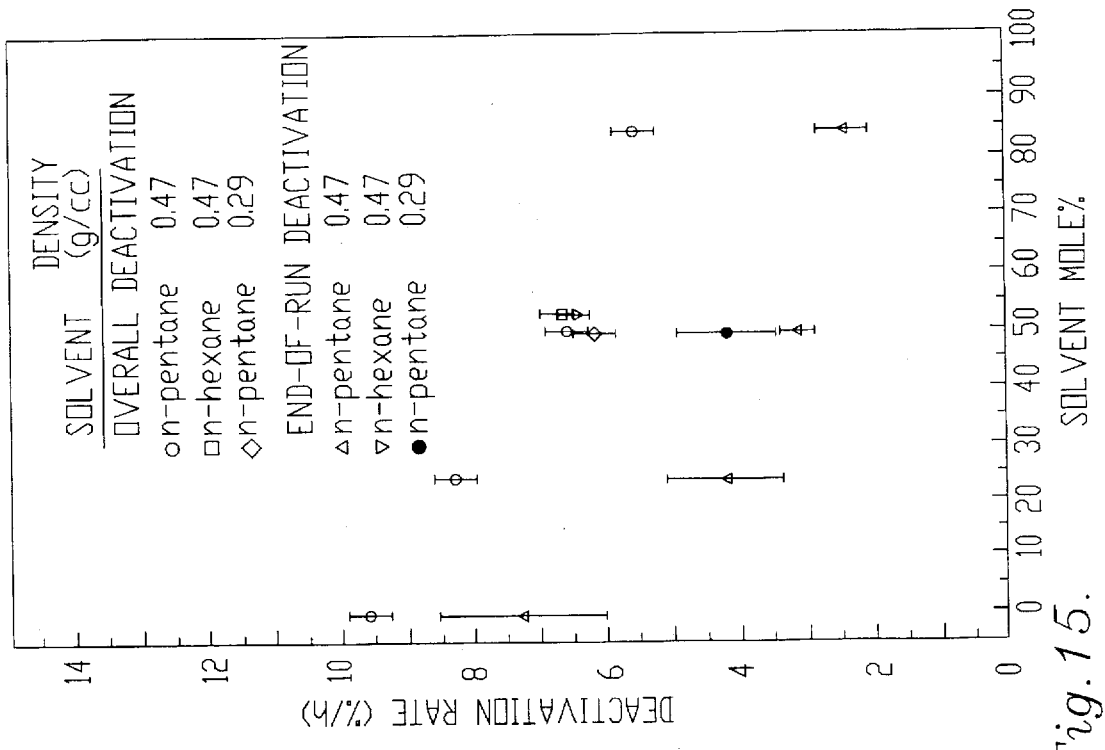
FIG. 15 is a plot showing cosolvent effect on catalyst deactivation rates.

FIG. 15 shows the effect of cosolvent addition on the catalyst deactivation rate. The overall deactivation (defined as the % decrease between the 10 min. and 8 hr isomerization rates) decreased almost twofold, from 9.6 to 5.5%/h, when the cosolvent fraction was increased from 0 to 80 mole %. The corresponding decrease in the end-of-run deactivation rate (defined as the % decrease in the isomerization rates between six and eight hours) was threefold. While the overall deactivation rate at 50% cosolvent addition was virtually unaffected either at the lower density or by using n-hexane as the cosolvent, the end-of-run deactivation rates were 3.1, 4.2 and 6.4%/h for n-pentane at 0.47 g/cc (T=281° C., P=265 bar), n-pentane at 0.29 g/cc (T=281° C., P=86.5 bar) and n-hexane at 0.47 g/cc (T=281° C., P=226 bar), respectively. Thus, the use of higher density n-pentane as an inert cosolvent produces a significantly lower deactivation rate. This result is somewhat surprising considering the lower oligomer formation in the latter two cases (see FIG. 11) and may be explained based on reported evidence that transition metals catalyze hydrogen transfer from supercritical solvents such as n-pentane. It seems plausible that n-pentane can undergo dehydrogenation on the Pt metal. The transfer of the resulting hydrogen to the surrounding coke is facilitated by the dense supercritical reaction mixture. Hydrogen donation would soften the coke and facilitate the in situ extraction of the coke-forming compounds from the catalyst resulting in a lower deactivation rate.

In an attempt to determine if a steady catalyst activity can be attained with cosolvent addition, one experiment was run for an extended period of 14 hours. For a feed containing 80 mole % n-pentane, FIG. 9 shows the 1-hexene isomerization rate history at 281° C. and 296 bar (reaction mixture density of 0.47 g/cc) at a space velocity of 135 g feed/h/g cat. The reaction rate was observed to decrease throughout the entire run, dropping nearly 10% from 8 to 14 hours. Although a steady state was not achieved in this time period, the two hour deactivation rate decreased 60% from 2.5%/h between 6 and 8 hours to 1.5 %/h between 12 and 14 hours. Thus, for the run time examined, the catalyst continued to deactivate although at progressively lower deactivation rates.

Figure 11:
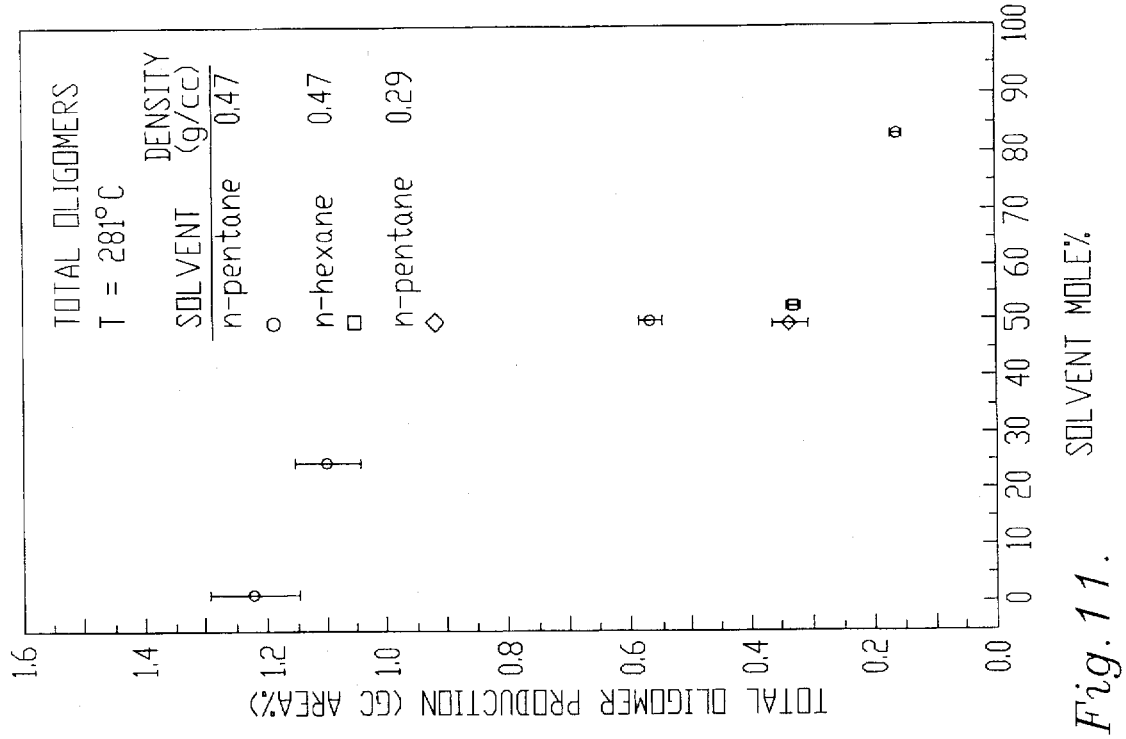
FIG. 11 is a plot showing cosolvent effect on hexene oligomer production.
Figure 17:
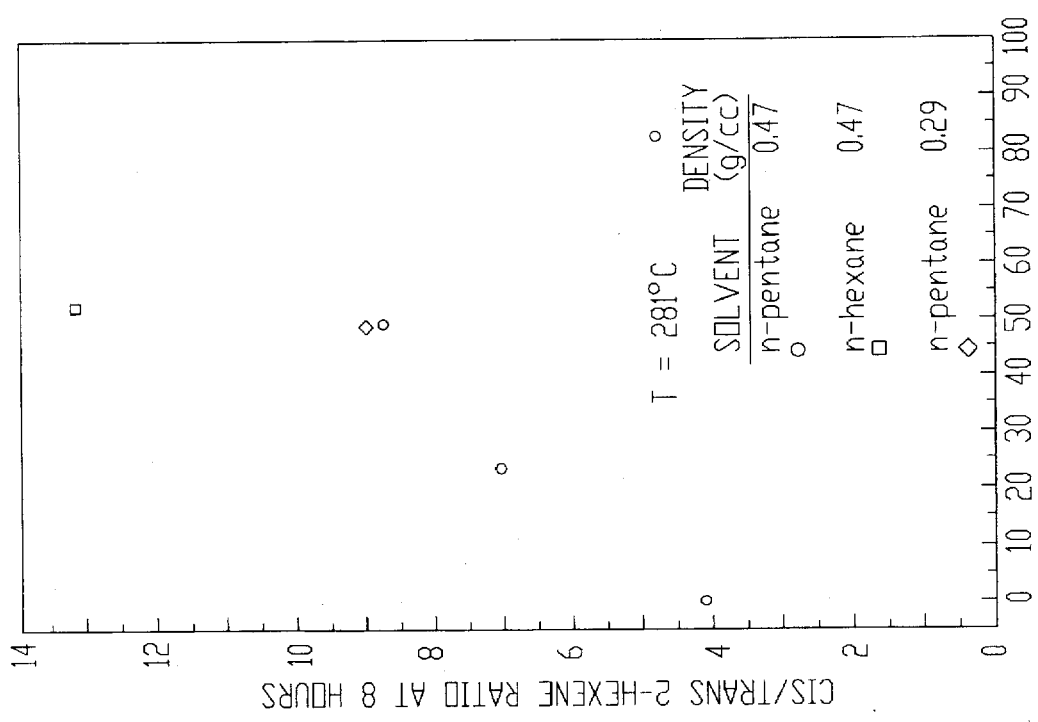
FIG. 17 is a plot showing cosolvent effect on 2-hexene/3-hexene selectivity.

FIG. 17 shows the effect of cosolvent addition on product selectivity. The 2- to 3-hexenes ratio followed the variation of the isomerization rate as observed with the pure hexene runs in Example 1; however, substantially higher selectivities were obtained in the presence of a cosolvent. The 2- to 3-hexenes selectivity ratio increased over twofold from 4.1 to 8.8 as the n-pentane fraction was varied from 0 to 50 mole %, and decreased to 4.8 as the cosolvent fraction was further increased to 80 mole %. At 50 mole % cosolvent fraction, while a decrease in the density had little effect on the selectivity ratio, the use of n-hexane produced a 50% increase in the ratio yielding a value of 13.2. Similarly, higher cis- to trans-2-hexene ratios were obtained in the presence of a cosolvent as shown in FIG. 11.

Figure 20:
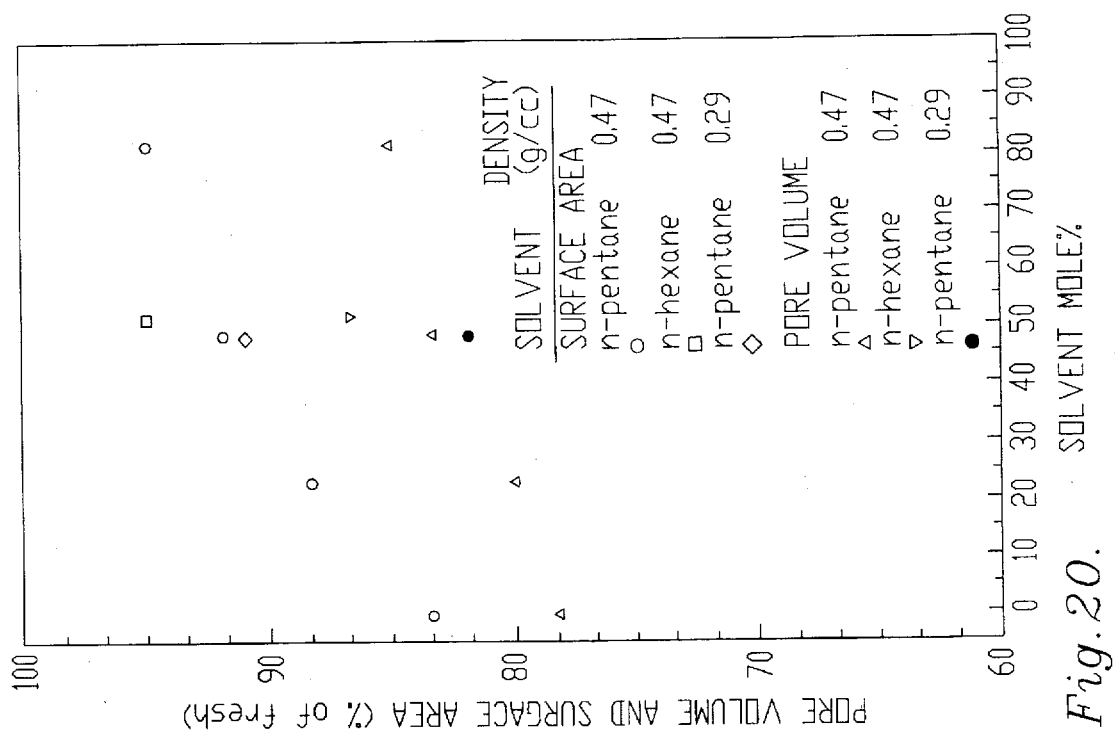
FIG. 20 is a plot showing cosolvent effect on end-of-run catalyst surface area and pore volume.
Figure 19:
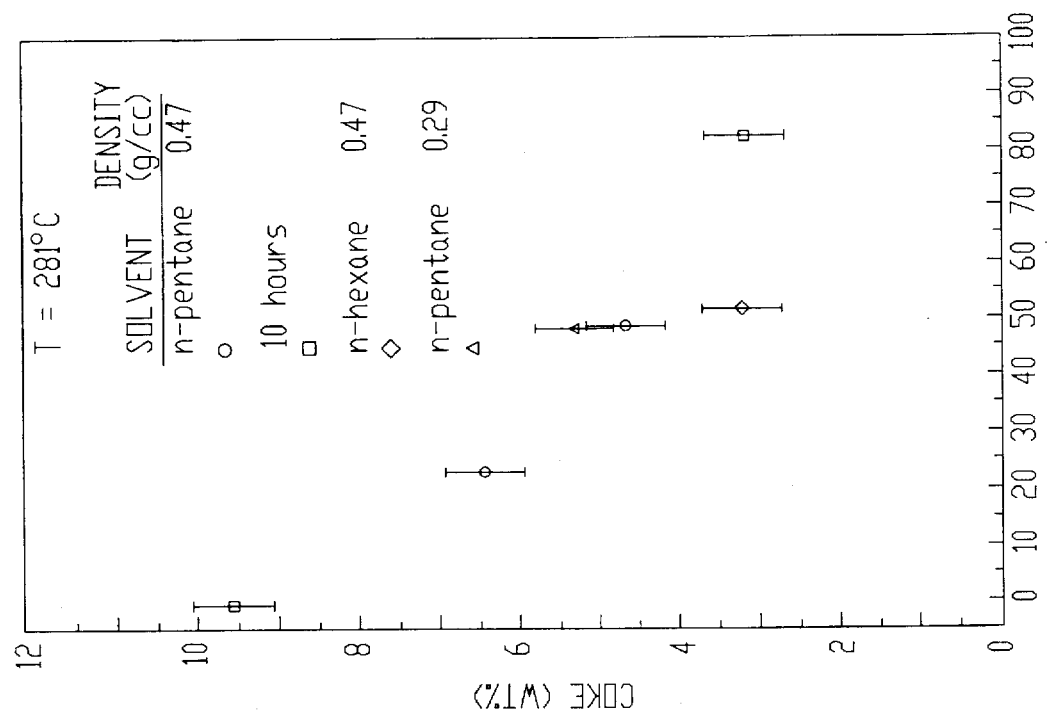
FIG. 19 is a plot showing cosolvent effect on end-of-run coke laydown.
Figure 22:
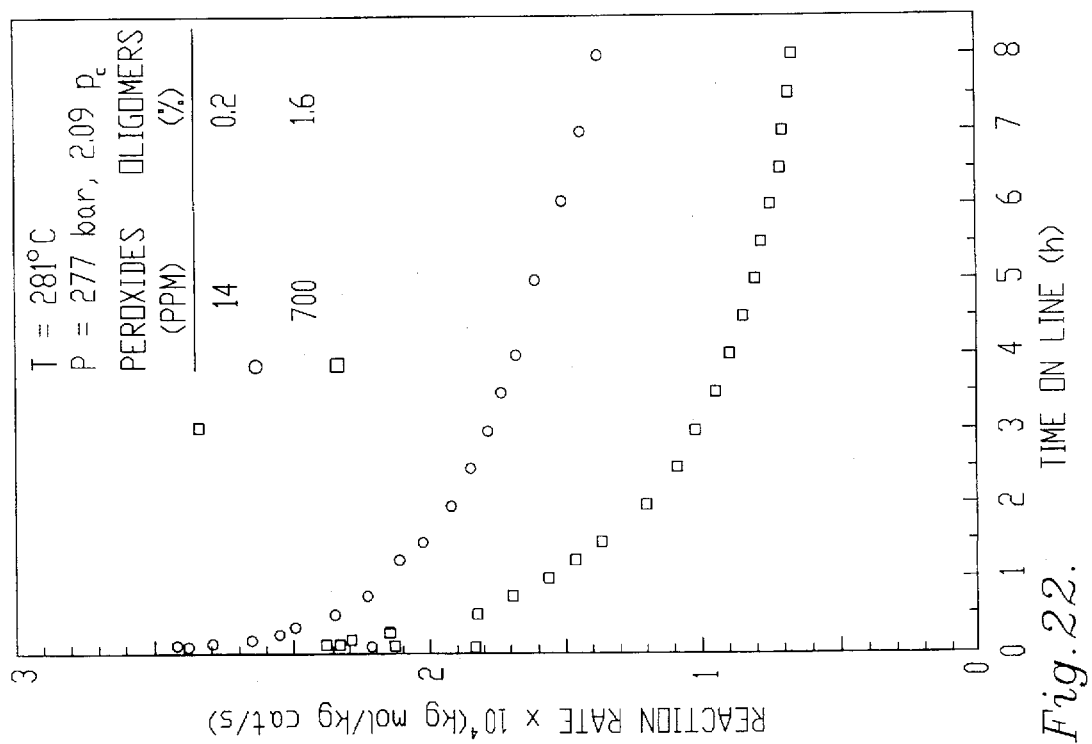
FIG. 22 is a plot showing effect of feed peroxide content on isomerization rate histories.
Figure 21:
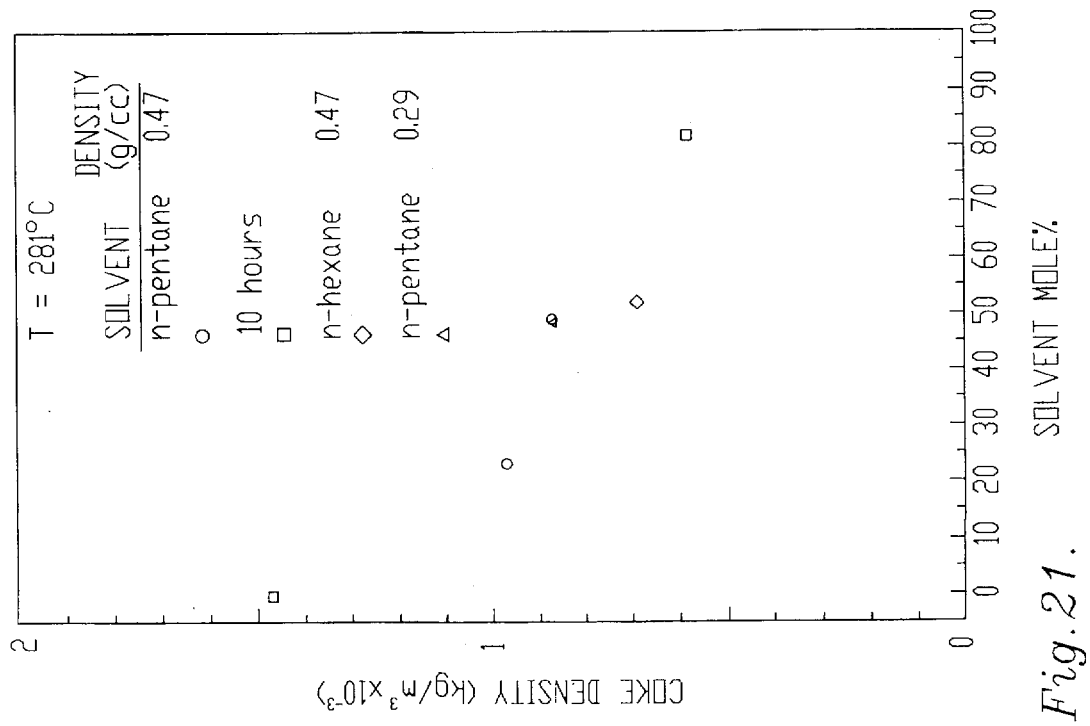
FIG. 21 is a plot showing cosolvent effect on coke density.

As seen in FIG. 19, coke laydown decreased over threefold as n-pentane addition increased from 0 to 80 mole % at a constant density of 0.47 g/cc. At 50 mole % cosolvent addition, coke laydown was lower when n-hexane was used as the cosolvent. As inferred from FIG. 20, the remaining surface area increased from 84 to 94% and the remaining pore volume increased from 78 to 85% as n-pentane fraction in the feed was increased from 0 to 80 mole %. Although the values at 50 mole % n-pentane addition were only mildly affected by a decrease in reaction mixture density, the pore volume and surface area improved noticeably when n-hexane was employed as the cosolvent. This improvement is consistent with the reduced coke laydown during the run. As shown in FIG. 21, coke density decreased from 1.5 to 0.6 g/cc when the cosolvent fraction was increased from 0 to 80 mole %. This decrease is attributed to lower oligomer concentrations (with lower average molecular weight) at higher cosolvent fractions (see FIG. 11), suggesting that both the amount as well as the average molecular weight of the oligomers influence the density (i.e., the chemical composition) of the coke.

Effect of Feed Peroxide Content on Oligomer Production and Catalyst Performance

The unexpected decrease in coke laydown when n-hexane instead of n-pentane was used as the cosolvent led us to analyze the two different 1-hexene sources used in these runs for possible impurities. Analysis by Ethyl Corporation (the suppliers) revealed a significant difference in peroxide concentrations between the two hexene feedstocks. The peroxide content was determined by sodium thiosulfate titration following a contacting step with sodium iodide. The hexene from lot# 851201, used for the majority of experiments, contained 700 ppm peroxide, while hexene from lot# PT 060592 contained 14 ppm peroxide, as ppm oxygen.

Given that organic peroxide radicals aid polymerization, the two feeds were examined separately by flowing each at approximately 136 g/h over 1 g of catalyst at 281° C. and 277 bar, yielding a supercritical density of 2.09 $\rho_c$. Under similar operating conditions, the 14 ppm peroxide feed (Lot # PT 060592) produced 0.2 wt % total oligomers, while the 700 ppm peroxide feed (Lot # 851201) produced 1.6 wt % total oligomers. The reaction rate histories are compared in FIG. 15 for the two feeds. The isomerization rate was higher throughout the run when the feed peroxide content was 14 ppm. A summary of reaction and deactivation rates is presented in Table 8. The initial (10 min.) isomerization rate increased 16% in the case of 1-hexene feed with reduced peroxide content, while the end-of-run (8 h) reaction rate increased over twofold. The overall deactivation rate decreased 65% and the end-of-run deactivation rate decreased 19% in the case of the low peroxide feed when compared to the high peroxide feed. As summarized in Table 9, the corresponding coke laydown decreased roughly ninefold with over 90% maintenance of the pore volume and surface area. The coke density decreased by roughly fourfold with a decrease in feed peroxide content (i.e., in oligomer production) reinforcing the dependence of coke density on the amounts and average molecular weight of the oligomers. The improvements in isomerization rates, deactivation rates and catalyst properties accompanying lower oligomer production are consistent with the observed deterioration in these values when oligomers are added to the reactor feed (see Table 7).

TABLE 8

Effect of Feed Peroxide Content on 1-Hexene Isomerization Rates and Catalyst Deactivation Rates at 281° C. and 277 bar

| Measured Quantity | 700 ppm Peroxides | 14 ppm Peroxides |
|---|---|---|
| Total oligomer production (5) | 1.6 | 0.2 |
| Initial reaction rate (kg mol/kg cat/s × 10⁴) | 2.29 | 2.66 |
| End-of-run (kg mol/kg cat/s × 10⁴) | 0.64 | 1.35 |
| Overall deactivation rate (%/h) | 9.2 | 6.3 |
| End-of-run deactivation rate (%/h) | 5.8 | 4.7 |

In industrial practice, the 1-hexene feedstock is typically passed over a bed of activated alumina to reduce peroxide content and stored in containers blanketed with nitrogen to prevent exposure to oxygen. To determine the effect of peroxide content on hexene oligomer formation, hexene feeds at four different peroxide levels were subjected to blank runs with the reactor operated at 281° C., 277 bar (yielding a supercritical density of 2.09 $\rho_c$) and a feed flow rate of 135 g/h.

Hexene feeds with 14 and 700 ppm peroxides were provided from hexene lots# PT 060592 and 851201, respectively. Peroxides were reduced to 2 ppm bypassing hexene from lot # PT 060592 over 50 g of dry activated neutral alumina at a flow rate of approximately 200 g/h. Peroxides were increased to 21 ppm by stirring the hexene from lot # PT 060592 in the presence of air for 68 hours. All samples were degassed in a mild vacuum following treatment to improve pump efficiency, and the feed vessels were allowed to be in contact with air during the non-catalytic experiments.

TABLE 9

Effect of Feed Peroxide content on Properties of Catalyst Coked at 281° C. and 277 bar

| Catalyst Property | Pretreated catalyst | 700 ppm Peroxides | 14 ppm Peroxides |
|---|---|---|---|
| Coke laydown (wt %) | — | 8.7 | 1.0 |
| BET Surface area (m²/g) | 174.9 | 141.5 | 170.0 |
| Pore volume (cc/g) | 0.440 | 0.335 | 0.398 |
| Coke density (g/cc) | — | 1.1 | 0.3 |

Bulk phase oligomer production for the various feed peroxide levels is shown in Table 10. Oligomer amounts are based on three samples taken at 30 minute intervals after the reactor reached steady state. Oligomer production increased with peroxide content, with total oligomers increasing almost 22 times from the alumina treated hexene (2 ppm peroxide content) to the untreated hexene in lot# 851201 (100 ppm peroxide content). The corresponding increases in the dimer, trimer, tetramer and pentamer formation rates are 12, 15, 39, and 150 times, respectively. As noted earlier, the higher-molecular-weight oligomers are more prolific coke producers and lead to rapid deactivation.

TABLE 10

Effect of Feed Peroxide Content on Blank Oligomer Production at 281° C. and 277 bar

| Feed peroxide (ppm) | Oligomer Production (GC area %) | | | | |
|---|---|---|---|---|---|
| | Dimer | Trimer | Tetramer | Pentamer | Total |
| 2 | 0.037 | 0.024 | 0.015 | 0.002 | 0.077 |
| 14 | 0.047 | 0.032 | 0.021 | 0.003 | 0.102 |
| 21 | 0.054 | 0.037 | 0.027 | 0.005 | 0.123 |
| 700 | 0.43 | 0.36 | 0.58 | 0.30 | 1.67 |

Except with the feed containing 2 ppm peroxides, the total oligomer production reached a steady state in the other cases. In the former case, total oligomers increased 36% from 0.066% to 0.089% over the one hour sampling time. The alumina-treated hexene was in contact with air in the reactor feed vessel during the blank runs. Following the alumina treatment and just prior to the runs, the hexene was degassed in a mild vacuum. Hence, it seems plausible that the oxygen was absorbed into the feed material during the course of the experiment, and that the peroxide level in the reaction mixture increased with time. It seems unlikely that the peroxide level increased in the feed vessel itself, since the increase in peroxide level during storage of hexene lot# 851201 corresponds to a total oligomer increase of only $5\times10^{-5}$%/h. This rate is two to three orders of magnitude slower compared to the increase in oligomer formation during the experiment with alumina pretreated feed. More likely, as oxygen was absorbed by the feed mixture, peroxides were formed rapidly in the high pressure, high temperature reactor leading to increasing oligomer formation with time. These results clearly bring out the importance of removing peroxides from olefinic feeds, especially in high pressure processing over acid catalysts.

CONCLUSIONS

During investigations of 1-hexene isomerization on a Pt/γ-$Al_2O_3$ catalyst, hexene oligomers are found to form in the fluid phase. These oligomers are significant coke precursors, increasing the coke formation and catalyst deactivation rates. The total amount and average molecular weight of the oligomers increased with isothermal increases in pressure from subcritical to supercritical values increasing the density of the coke.

The dilution of the feed with an inert cosolvent such as n-pentane at a constant supercritical density and space velocity reduces oligomer concentrations while maintaining the in situ extraction capability of the coke-compounds. Hence, coke laydown is significantly reduced. Consequently, the isomerization rate increases and deactivation rate decreases. Although oligomer formation continues to decrease with cosolvent addition, the isomerization rate eventually becomes limited by the low feed concentrations of 1-hexene and hence passes over a maximum.

It was determined that ppm levels of organic peroxides in the hexene feed, formed as a result of exposure to air during either storage or the experiments, aid the formation of hexene oligomers in the fluid phase. The feed peroxide content can be reduced by pretreating the feed with activated alumina. For reactor operation at 281° C. and 277 bar (2.09 $\rho_c$), this pretreatment resulted in the virtual elimination of the peroxides and an eightfold decrease in total oligomer concentration at a space-velocity of 135 g/h/g cat. Consequently, increased isomerization rates and significantly lower deactivation rates are attainable.

Our results indicate that peroxide removal from the feed and cosolvent addition can significantly improve catalyst activity maintenance and pore accessibility in supercritical reaction mixtures.

EXAMPLE 3

Oligomer Formation Curtailed by Removing Peroxide Impurities from Feed Stock

Example 3 demonstrates that the oligomer formation in the fluid phase may be curtailed by removal of peroxide impurities from the feed stock by means of passing the feed stock through an alumina trap, or other suitable adsorption media.

Experimental Procedures

The isomerization of 1-hexene over 1/16" Pt/γ-$Al_2O_3$ (Engelhard E-302) reforming catalyst was investigated. The Pt loading on the catalyst is 0.6 wt %. The catalyst was first pretreated in flowing nitrogen at 100 sccm in a pretreatment reactor at 330° C. for 18 h, followed by hydrogen at 100 sccm at 330° C. for four h. The pretreated catalyst was found to have a BET surface area of 175 $m^2$/g, total pore volume of 0.44 $cm^3$/g and an average pore radius of roughly 50 Å. One gram of the pretreated catalyst was loaded into the reactor and the 1-hexene isomerization was investigated at 281° C. (1.1 $T_c$) and at pressures yielding subcritical to supercritical conditions (0.2–2.2 $\rho_c$). Table 1 lists the operating pressures and the estimated reaction mixture densities at the various pressures. As in the previous studies, a space velocity of approximately 135 g hexene/g cat./h was used for all the runs.

Figure 23:
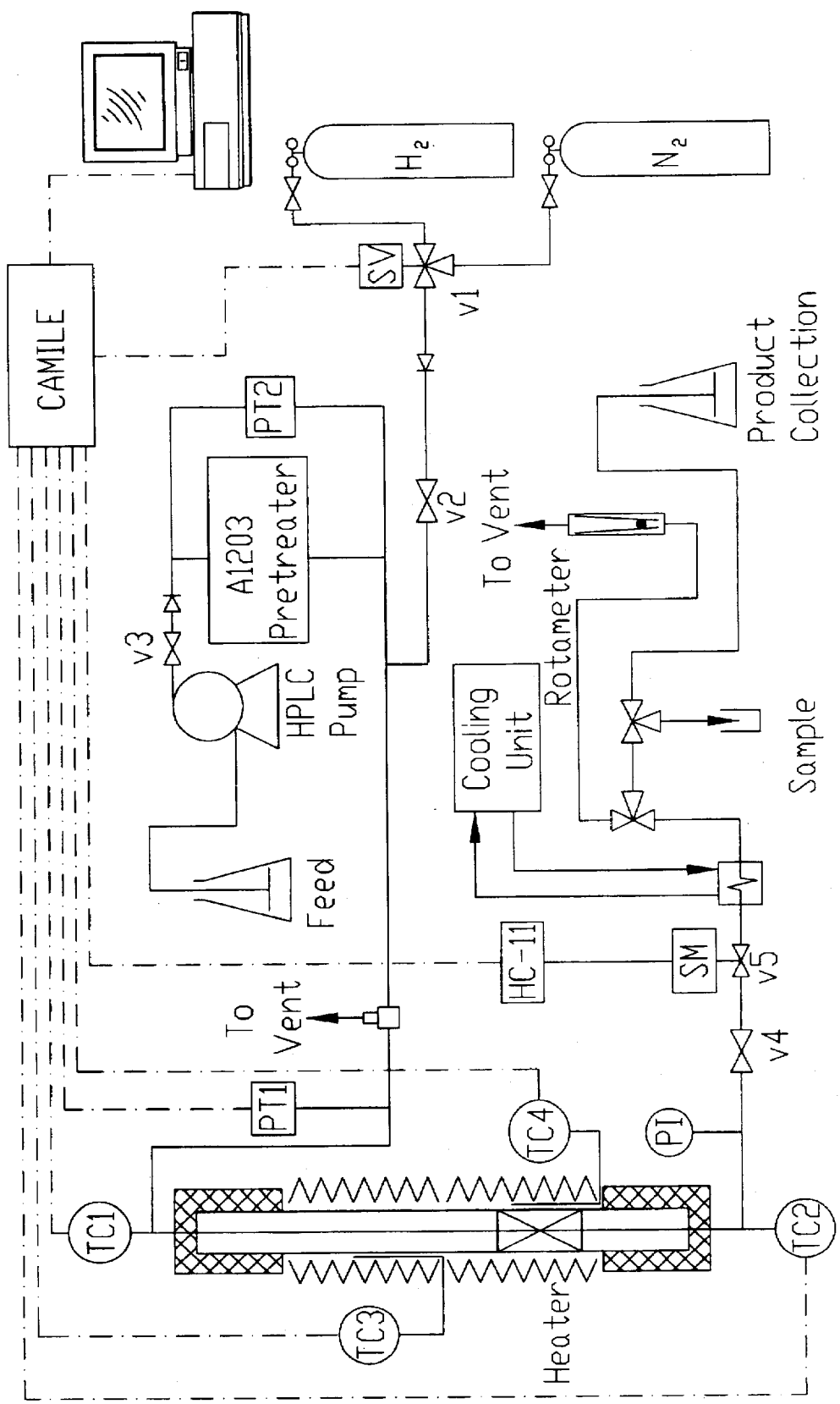
FIG. 23 is a schematic of the experimental unit employed in Example 3.

FIG. 23 shows a schematic of the high pressure experimental unit. The feed section consists of a liquid feed supply bottle connected to an HPLC pump (Waters' Associates #6000A) capable of delivering constant flow rates between 6 and 600 ml/h against pressure heads up to 400 bar. The feed section was also able to provide either hydrogen or nitrogen gas (for catalyst pretreatment or system purging) to the experimental unit. The choice of nitrogen or hydrogen gas is selected via a three-way solenoid valve (V1) controlled by the Camile 2500 data acquisition and control system. Either liquid or gas feed is selected by manually opening either valves V2 or V3 respectively.

The 1-hexene (Ethyl Corporation; Lot # PT 060592) feed is pumped through a 1' long stainless steel tube (roughly 0.8 cm i.d.) containing 11.6 grams of dry activated neutral alumina which is used to adsorb organic peroxides from the hexene feed. The pressure drop across the alumina bed is monitored using a differential pressure transducer PT2 (1.4±0.007 bar). The liquid is then passed via a high pressure line filter fitted with a 10 μm frit, before passing through a safety head equipped with a rupture disc rated to a burst pressure of 400 bar at 20° C.

The feed enters the top of a vertically mounted stainless steel tubular reactor (15 ml capacity) and passes over a 3.5 cm long catalyst bed located approximately 10.5 cm from the bottom of the reactor. Thermocouples (J-type) are placed on each end of the catalyst bed to monitor and to provide feedback for PID control of the reactor temperature. The reactor effluent then passes through an Autoclave Engineers' 30VRMM micrometering valve ($C_v$=0.04). The micrometering valve is actuated via a microprocessor controlled stepper motor which forms part of the PID control loop for maintaining reactor pressure. A pressure transducer (400±1.9 bar) located upstream from the reactor provides feedback for the reactor pressure control loop. The nearly 14,000 steps from the fully-open to the fully-closed valve positions allows fine control of the reactor pressure. Sensitive pressure control is especially desirable along a near-critical isotherm at which small changes in pressure around the critical pressure can lead to relatively large changes in density and transport properties.

After passing through the micrometering valve the reactor effluent is cooled in a heat exchanger. A manually controlled three-way valve (VS) is used to either sample the liquid effluent for off-line analysis or collect it for safe disposal. Whenever purge gas is used in the setup, a manually controlled three way valve (V7) is used to direct the gas through a rotameter and to the vent. The reactor effluent was sampled at various times for off-line analysis of 1-hexene, its isomers and oligomers using an HP5890 GC/FID instrument. At the end of a run (typically lasting eight hours), the catalyst was removed and subjected to gravimetric analysis (to determine the amount of coke laydown) and micromeritics analysis (to determine the loss in surface area and pore volume due to coking) with a Gemini 2000 Pore Volume and Surface Area analyzer.

All the measurement and control devices in the reactor unit (viz., thermocouples, pressure transducers, stepping motor controls for driving the micrometering valves and heaters) are interfaced with the Camile 2500 Data Acquisition and Control Unit. Programmed sequences developed for reactor startup, operation and shutdown enhance the ability to accurately repeat experimental procedures.

RESULTS AND DISCUSSION

Figure 24:
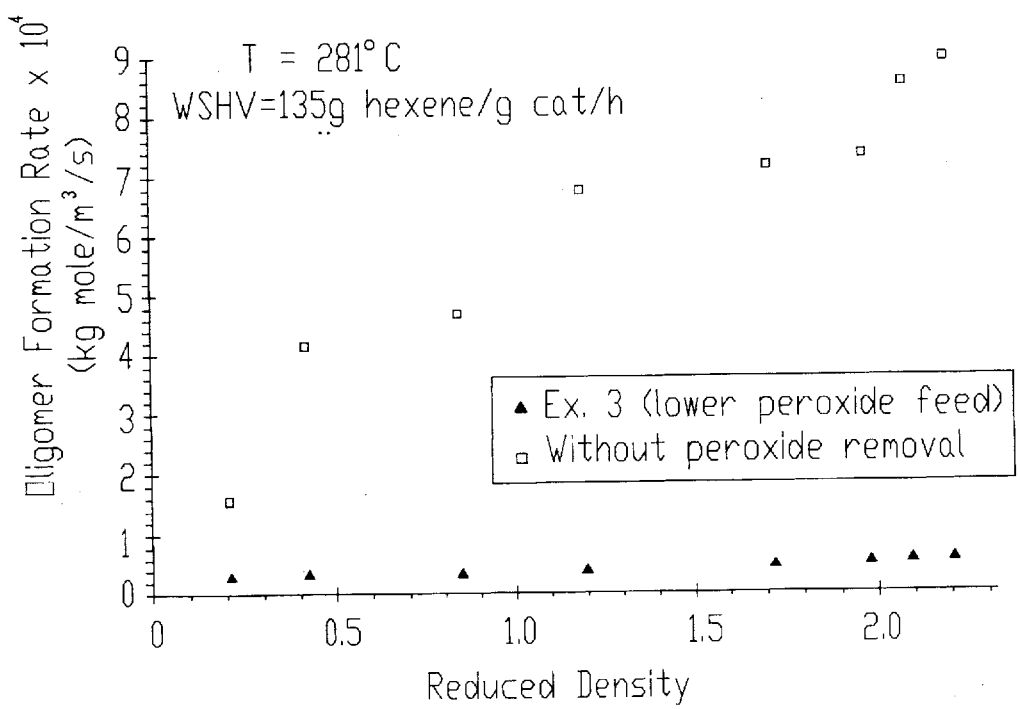
FIG. 24 is a plot showing a comparison between oligomer formation rates involving 1-hexene isomerization at a near-critical temperature versus time when 1-hexene is isomerized with and without peroxide reduction from the feed stock.

FIG. 24 compares hexene oligomer production rates obtained using a hexene feed containing 700 ppm organic peroxides with those obtained using on-line alumina pretreatment of the hexene feed. Analysis by sodium thiosulfate titration following a contacting step with sodium iodide indicated that the alumina pretreatment reduced the peroxide content from 700 to 2 ppm, expressed as ppm oxygen. In both cases, oligomer formation was measured in the absence of the Pt/γ-Al$_3$ catalyst. Tests for possible catalytic activity due to the reactor material of construction revealed that the oligomer formation rate was proportional to the residence time based on the homogeneous reactor volume and not on the reactor surface area. Virtually all the oligomer formation reported in FIG. 24 therefore occurred in the fluid phase catalyzed by organic peroxide radicals.

It is evident from FIG. 24 that the peroxide reduction in the hexene feed by alumina pretreatment results in an approximately five-fold decrease in the oligomer production rate at the lowest subcritical density (0.2 $\rho_c$) and an 18-fold decrease at the highest reduced density (2.2 $\rho_c$). In the density range investigated, while the total oligomer production rate increased twofold in the case of the alumina-pretreated feed, the corresponding increase is fourfold when using untreated 1-hexene containing about 700 ppm peroxide. Reducing the oligomer formation in the fluid phase has a positive effect on catalyst performance as shown in FIG. 3. At a supercritical density of 1.20 $\rho_c$ (70 bar, 281° C.), the initial (10 min.) and end-of-run (8 h) isomerization rates were about 25% and 250% higher respectively when the peroxide content is lowered. It can also be seen from FIG. 3 that the catalyst deactivation rate (i.e., the decline of the isomerization rate with time) was more pronounced in the case of the higher peroxide feed.

Figure 26:
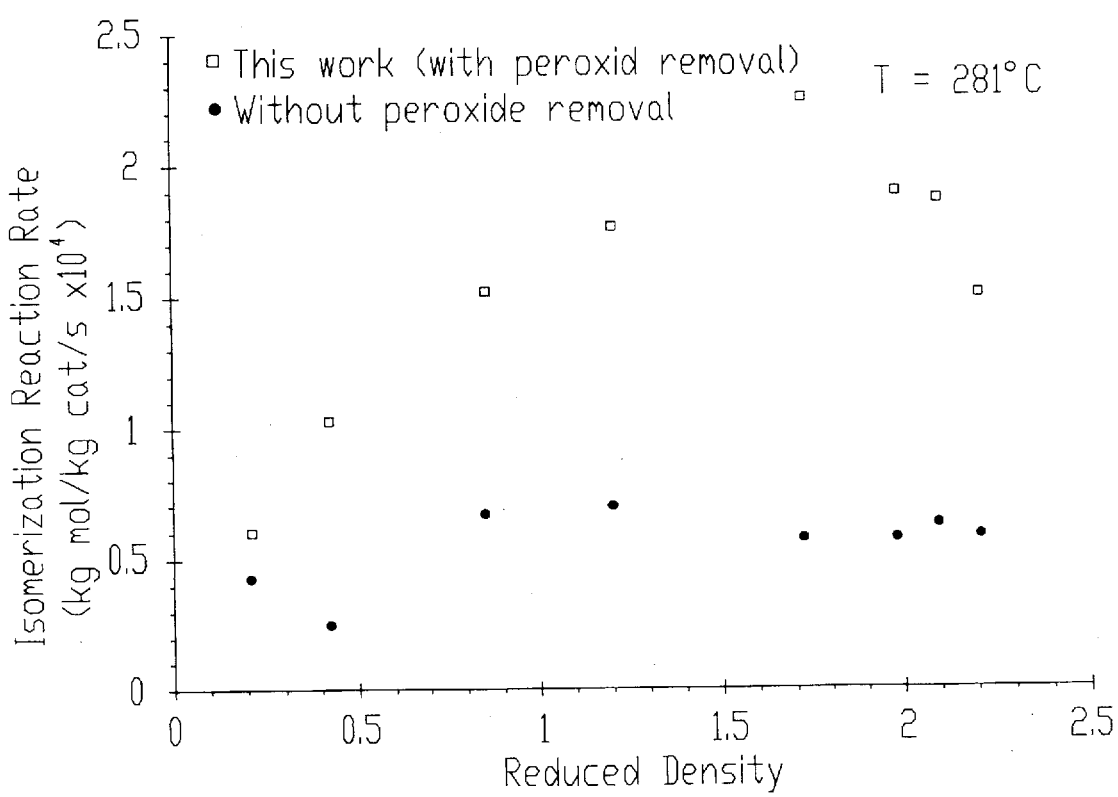
FIG. 26 is a plot showing a comparison between isomerization reaction rates involving 1-hexene isomerization at a near-critical temperature as a function of reduced density in feed stocks with and without peroxide reduction.
Figure 29:
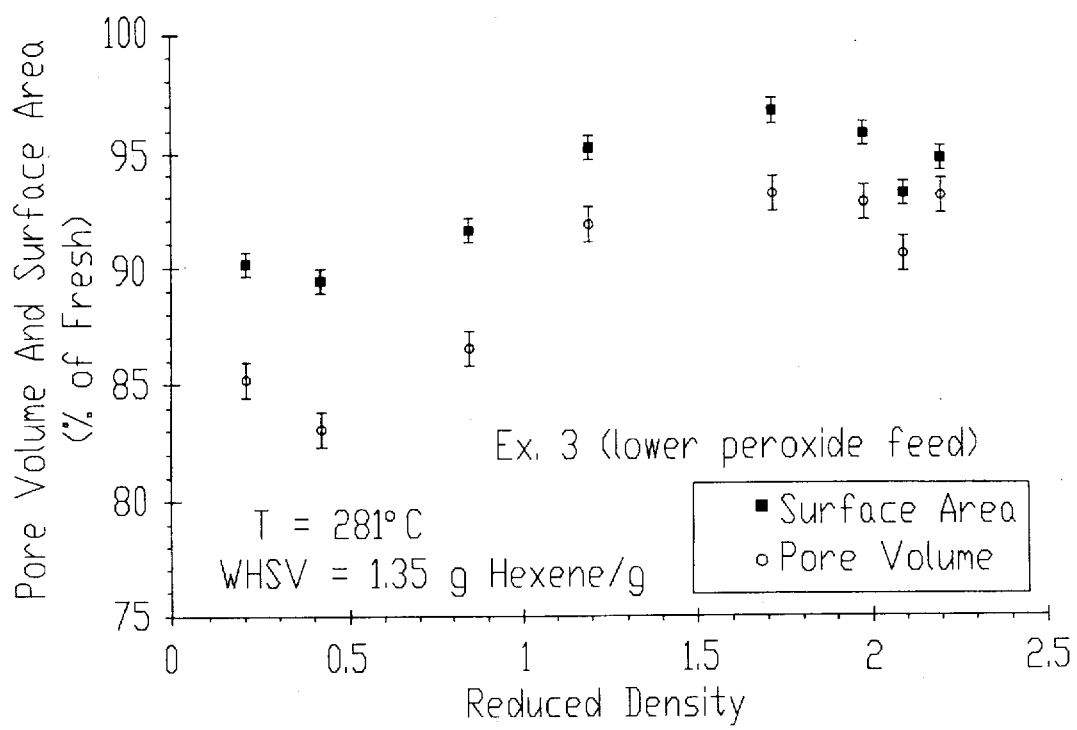
FIG. 29 is a plot showing a comparison between pore volume and surface area on catalyst used to isomerize 1-hexene at a near-critical temperature as a function of reduced density in feed stocks with peroxide reduction.
Figure 28:
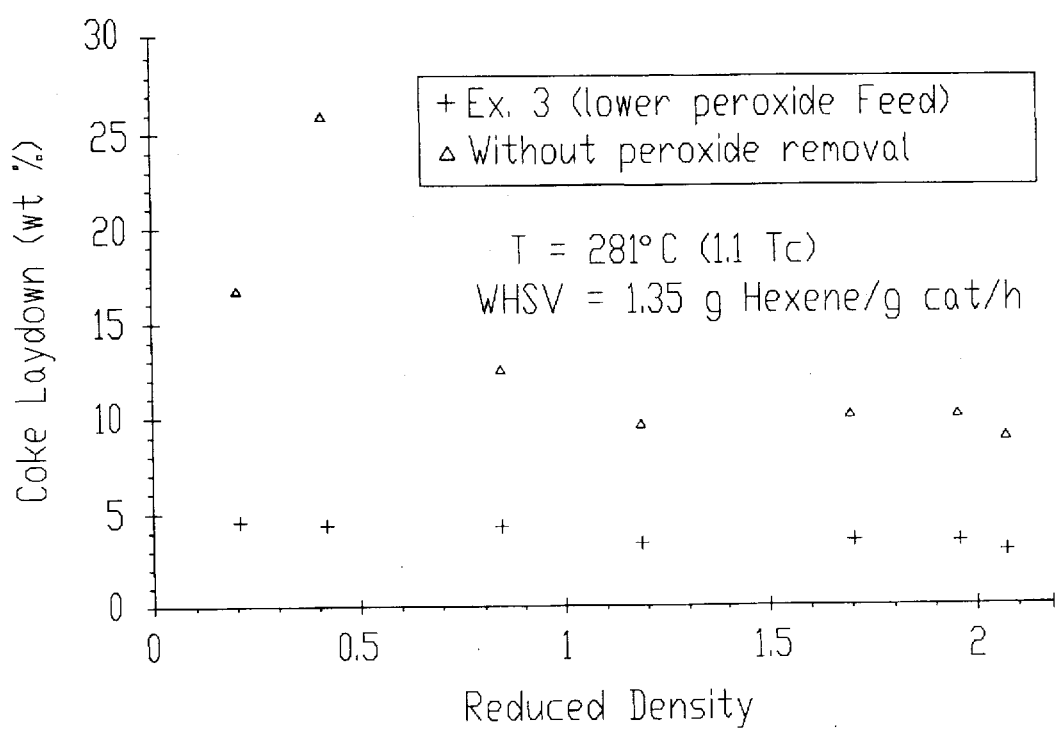
FIG. 28 is a plot showing a comparison between coke laydown on catalyst used to isomerize 1-hexene at a near-critical temperature as a function of reduced density in feed stocks with and without peroxide reduction.

The beneficial effect of on-line alumina pretreatment of the hexene feed (i.e., of reducing hexene oligomer formation in the fluid phase) on catalyst performance was observed in the subcritical as well as in the supercritical runs. As seen in FIG. 4, end-of-run (8 h) isomerization rates in supercritical reaction mixtures were up to an order of magnitude higher in the case of the alumina-pretreated hexane compared to the lowest rate obtained with the higher peroxide feed. In the former case, the end-of-run isomerization rates increased almost fourfold as the reaction mixture density is increased from subcritical (0.2 $\rho_c$) to supercritical (1.7 $\rho_c$) values. The corresponding increase was only 60% without peroxide removal. In both cases, the isomerization rates increase with isothermal increases in reaction mixture density from subcritical to supercritical values and eventually decrease with further increases in density in the supercritical region (FIG. 26). As shown previously, the increase in the isomerization rates is due to the in situ extraction of the coke-forming compounds at near-critical conditions while the decrease in the isomerization rates at higher supercritical densities is due to pore-diffusion limitations in liquid-like reaction mixtures. However, the maximum in the isomerization rate occurs at about 1.7 $\rho_c$ in this work compared to roughly 1.2 $\rho_c$ in the previous work. In the absence of alumina pretreatment, the peroxides in the hexene feed cause the oligomer formation rates to increase more sensitively with pressure (FIG. 24). This results in increased coke buildup in the pores leading to diffusion limitations and therefore to decreased isomerization rates at higher densities.

Figure 27:
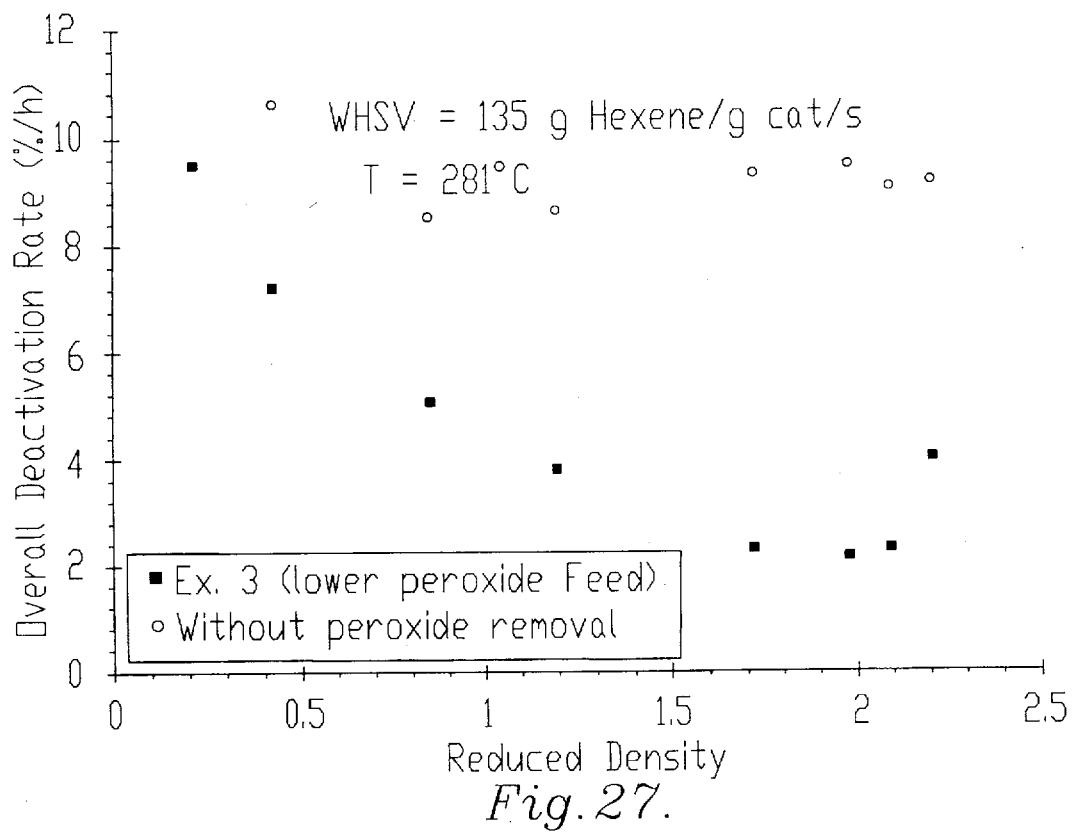
FIG. 27 is a plot showing a comparison between overall deactivation rates involving 1-hexene isomerization at a near-critical temperature as a function of reduced density in feed stocks with and without peroxide reduction.

As shown in FIG. 27, alumina pretreatment of the feed results in over a fivefold decrease in the overall deactivation rates (expressed as the % decrease in the isomerization rates between 10 min. and 8 h) as the reaction mixture density is increased from 0.2 to 1.7 $\rho_c$. In sharp contrast, the results obtained without alumina pretreatment of the feed indicate only a slight improvement in deactivation rates at supercritical conditions. Also observed in FIG. 27 is that the minimum deactivation rates obtained for this work occurred around the same density range (1.7–2 $\rho_c$) in which the isomerization rate reaches a maximum (FIG. 26). These results clearly illustrate that the reduction of peroxides in the 1-hexene feed significantly improves isomerization rates while simultaneously decreasing the overall catalyst deactivation rates, especially at supercritical conditions.

Gravimetric measurements of the catalyst at the end of each run revealed that without alumina pretreatment, the coke laydown increased to a maximum value of 26 wt % at subcritical conditions and decreased to a minimum value of 7.3 wt % at supercritical conditions (FIG. 24). In contrast, the maximum coke laydown when using on-line alumina pretreatment of the 1-hexene feed was only 4.5 wt %, even at subcritical conditions, and decreased to a minimum value of 2.1 wt % at supercritical conditions. Micromeritics analysis (by nitrogen physisorption) revealed that more than 90% of the initial catalyst surface area and pore volume are accessible in catalysts exposed to supercritical reaction mixtures. These results provide clear evidence that the on-line alumina treatment of the 1-hexene feed significantly reduces coke laydown and improves pore accessibilities in supercritical reaction mixtures. Consequently, isomerization rates are increased and catalyst deactivation by coking is mitigated.

The foregoing results are significant considering that many acid-catalyzed reactions such as isomerization and alkylation reactions involve olefinic feeds. In such cases, ppm levels of organic peroxide radicals can form during exposure to air. These peroxide radicals catalyze the formation of olefinic oligomers in the fluid phase, which are major coke precursors. The results prove that removal of the peroxides by on-line pretreatment of the olefinic feed with activated alumina can lead to significant improvements in catalyst activity maintenance at supercritical conditions. At 281° C. and a space velocity of 135 g/h/g cat, a relatively moderate increase in operating pressure from 22 bar (0.21 $\rho_c$) to 53 bar (0.85 $\rho_c$) results in a 250% increase in the isomerization rates and a twofold decrease in the catalyst deactivation rate.

Figure 25:
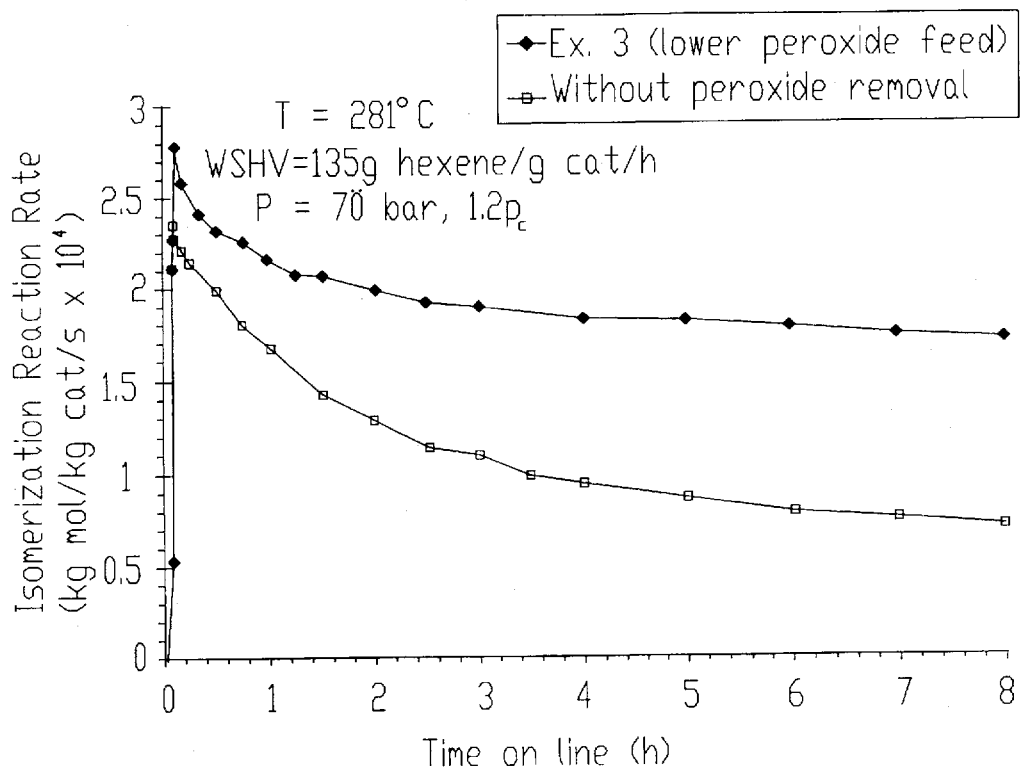
FIG. 25 is a plot showing a comparison between isomerization reaction rates involving 1-hexene isomerization at a near-critical temperature versus time when 1-hexene is isomerized with and without peroxide reduction from the feed stock.

It should be clear from FIG. 25 that the deactivation rate is highest during startup, which is performed as follows. With the reactor held at the operating temperature at 281° C., the 1-hexene feed is pumped into the 15 ml reactor at a flow rate such that the critical density was reached or passed in two minutes in all the experiments. Yet, this relatively rapid startup could not prevent the formation of consolidated, unextractable coke during the subcritical phase of pressure buildup. Recent studies indicate that dilution of the hexene feed with an inert cosolvent like n-pentane, such that the reaction mixture is at supercritical conditions, reduces coke precursor concentrations (and thereby the coke formation rates) while maintaining the in situ extraction of the coke-forming compounds. Consequently, catalyst deactivation rate is significantly reduced. We are currently investigating the addition of inert cosolvents such as n-pentane or n-hexane during reactor startup such that the reaction mixture is already in a supercritical state when the reactant (1-hexene) is introduced. This startup strategy could minimize or even eliminate catalyst deactivation during startup resulting in steady activity maintenance, when coke formation rates are balanced by the coke extraction rates.

CONCLUSIONS

Organic peroxides tend to form in olefinic feedstocks upon exposure to air. A few hundred parts per million of these impurities are sufficient to catalyze the formation of olefinic oligomers in the fluid phase. In the vicinity of the critical point, the oligomer formation increases sensitively with pressure. These oligomers are prolific coke precursors and cause extensive coking and catalyst deactivation at subcritical conditions. On-line adsorption of the peroxide impurities in a bed of activated alumina results in almost total removal of the peroxides. For the Pt/γ-Al$_2$O$_3$ catalyzed isomerization of 1-hexene, such pretreatment of the hexene feed significantly improves catalyst performance, especially in supercritical reaction mixtures. Coke laydown is significantly reduced resulting in improved pore accessibilities. Consequently, isomerization rates and catalyst deactivation rates are improved several fold relative to subcritical reaction mixtures. The results suggest that the process can be further improved by using an inert cosolvent (i.e., one that does not form coke on the catalyst) such as n-pentane to fill up the reactor during startup such that the reaction mixture is supercritical when the olefinic feed is introduced. Such a process would minimize the buildup of consolidated, unextractable coke during the subcritical portion of reactor fillup and could lead to enhanced activity maintenance at supercritical conditions.

The results show that supercritical reaction media can be used to mitigate coke buildup and thereby extend catalyst life in certain industrially important isomerization and alkylation reactions on porous acid catalysts such as zeolites. Thus, in accordance with the instant invention, inert cosolvents may be employed to establish reactor startup to desired supercritical conditions by contacting the inert cosolvent stream with the catalyst under conditions at a temperature of at least the critical temperature and pressure of the cosolvent. The cosolvents useful in the practice of the invention include those having a critical temperature between 1.01–1.2 T$_c$ of the product stream and having a critical pressure between 1–3 P$_c$ of the product stream.

EXAMPLE 4

Catalytic Dehydrogenation of Endothermic Fuels In a Membrane Reactor at Supercritical Conditions A unique set of problems arise when employing enhanced in situ extraction of coke compounds by means of near-critical and supercritical reactor operating conditions of the instant invention when the catalyzed reaction involved is a dehydrogenation reaction. The presence of hydrogen in the reaction mixture (which can be up to 60 mol % in the case of methyl cyclohexane conversion to toluene and hydrogen over a Pt/γ-Al$_2$O$_3$ catalyst) renders the attainment of liquid-like densities extremely difficult.

Thus, the instant invention employs membrane reactors in which the catalyst pellets are housed in a reactor vessel to which the hydrocarbon feed stock reactants are fed. In the case of methyl cyclohexane dehydrogenation, the reaction is carried out in such a reactor and the product hydrogen gas is separated form the reaction mixture by preferential diffusion across a porous membrane such as γ-alumina placed in the reactor, and is swept away by an inert gas such as helium flowing in the membrane tube referred to as the permeate side. The reactor side is isolated from the permeate side by the membrane wall. The remaining reaction mixture, consisting mostly of unreacted methyl cyclohexane (P$_c$=34.26 atm; T$_c$=298.87° C.) and toluene (P$_c$=41.6 atm; T$_c$=320.6° C.), can be easily maintained in a dense supercritical state. In addition to alleviating thermodynamic limitations to the methyl cyclohexane conversion, the selective removal of hydrogen from the reaction zone also makes it easier to maintain dense reaction mixtures. The supercritical reaction mixture then mitigates coke formation on the catalyst pellets according to Example 1. This method is also applicable to the case where the membrane itself contains the catalyst.

The invention may also be practiced in connection with Fischer-Tropsch (FT) and alcohol synthesis reactions, and other hydrogenation reactions which are highly exothermic. Consequently, when such reactions are carried out in a gas-phase in a fixed bed reactor, hot spots may form in the catalyst bed leading to deactivation of the catalyst by formation of carbon and by sintering. Additionally, these reactions may produce low volatile, high molecular weight hydrocarbons (or wax) that accumulate on the catalyst surface and eventually lead to pore-plugging. In order to provide better heat transfer and temperature control, a slurry phase technology (the LPMeOH process) in which catalyst particles are suspended in mineral oil was developed for methanol synthesis. A similar technology was also developed for FT synthesis. However, reduced diffusivities in liquid-filled pores causes the overall reaction rate in the slurry-phase reaction to be much lower than in the case of the gas-phase reaction. In the case of methanol synthesis, the syngas conversion is also limited by thermodynamic equilibrium due to accumulation of methanol in the reaction zone. Clearly, the ideal reaction medium for the exothermic syngas conversion processes should possess liquid-like densities and heat capacities for efficient product desorption and heat removal, yet gas-like diffusivities for enhanced product removal and reaction rates. Near-critical reaction media operations in accordance with the instant invention offer such a unique combination of physical and transport properties.

While a near-critical solvent has a liquid-like density and solvent power, the transport properties (momentum, thermal and mass diffusivities) are intermediate to that of a gas and a liquid. In the vicinity of the critical point, these physical properties can be continuously varied between gas-like and liquid-like properties with relatively small changes in pressure and/or temperature. Thus near-critical reaction media offer an optimum combination of solvent and transport properties that is better suited than either gas-phase or liquid-phase reaction media for efficient heat removal and for enhanced transport rates of reactants/products in the catalyst pores. The easily-tunable densities of near-critical media (with relatively small variations in pressure) may thus be exploited for varying the relative transport rates of products and, therefore, for manipulating product selectivity. In the case of methanol synthesis, enhanced removal rates of methanol from the reaction zone should also alleviate thermodynamic limitations to syngas conversion. In addition, the ability of near-critical media to extract catalyst deactivating agents such as carbonyl species in situ enhances catalyst activity maintenance.

We claim:

1. A method to minimize catalyst deactivation rate and coke laydown, and maximize desired reaction rate in hydrocarbon processing, comprising:

providing a feed stream including hydrocarbon feed stock components;

pretreating said feed stream to reduce peroxide content;

establishing reactor startup conditions by contacting an inert cosolvent stream with a quantity of catalyst at a desired catalyst temperature of 1.0–1.2 critical temperature of said cosolvent stream and at a pressure between the critical pressure of said cosolvent stream and a pressure necessary to establish the fluid density of the cosolvent stream of not more than 0.65 gm/cc;

thereafter contacting said feed stream with said catalyst to generate a reaction mixture stream including formed reaction products, inert cosolvents, and hydrocarbon reactants under supercritical conditions, said contacting at a desired catalyst temperature of about 1–1.2 critical temperature of the resulting reaction mixture and at a pressure between the critical pressure of the reaction mixture and a pressure necessary to establish said reaction mixture fluid density of greater than 0.65 gm/cc.; and separating the products, reactants and inert cosolvent in said product stream by isothermal, stepwise, pressure reduction.

2. In a method of carrying out a catalyzed reaction subject to catalyst deactivation by coke formation on the reaction catalyst including the steps of providing a feed stream including a reactant for the reaction and impurities comprising peroxide impurities, contacting said feed stream with a solid porous catalyst and causing the catalyzed reaction to occur and generate a reaction mixture, the improvement which comprises the steps of pretreating said feed stream to remove at least a portion of said peroxide impurities from said feed stream prior to said contacting step for lessening the amount of said catalyst deactivation by coke formation on the catalyst.

3. The method of claim 2, said catalyzed reaction being selected from the group consisting of hydrogenation, isomerization, alkylation, acylation, aromatic disproportionation, alcohol synthesis, and Fischer-Tropsch process reactions.

4. The method of claim 2, said reaction being a hydrocarbon processing reaction, said feed stream including $C_1$–$C_{20}$ hydrocarbon feed stock components therein.

5. The method of claim 2, said catalyst having a total surface area greater than 5 $m^2/g$.

6. The method of claim 2, including the step of carrying out said reaction at a catalyst temperature of from about 1.01–1.2 critical temperature of said reaction mixture.

7. The method of claim 2, including the step of adding a cosolvent to said feed stream.

8. The method of claim 7, said cosolvent being selected from the group consisting of n-pentane and n-hexane.

9. The method of claim 7, said cosolvent having a critical temperature below the catalyst temperature during said contacting step.

10. The method of claim 2, said pretreating step being carried out so that said feed stream contains less than about 100 ppm of said peroxide impurities.

11. The method of claim 2, said pretreating step comprising the step of contacting said feed stream with activated alumina.

12. The method of claim 2, said contacting step occurring at a catalyst temperature of about 1–1.2 critical temperature of said reaction mixture and at a pressure for establishing the fluid density of said reaction mixture at a level of from 0.05 to greater than 0.5 g/cc.

13. In a method of caring out a catalyzed reaction subject to catalyst deactivation by coke formation on the reaction catalyst including the steps of providing a feed stream including a reactant for the reaction and inherent impurities therein comprising peroxide impurities, contacting said feed stream with a solid porous catalyst and causing the catalyzed reaction to occur and generate a reaction mixture, the improvement which comprises the steps of employing a feed stream having less than about 100 ppm of said inherent peroxide impurities therein for lessening the amount of catalyst deactivation by coke formation on the catalyst.

14. The method of claim 13, said contacting step being carried out at a catalyst temperature of about 1–1.2 critical temperature of said reaction mixture and at a pressure for establishing the fluid density of said reaction mixture at a level of from 0.05 to greater than 0.5 g/cc.

* * * * *